United States Patent
Olivas et al.

(12) 
(10) Patent No.: US 6,495,744 B2
(45) Date of Patent: Dec. 17, 2002

(54) SUN DEVIL LETTUCE VARIETY

(75) Inventors: Nathan K. Olivas, Salinas, CA (US); Nathan J. Olivas, Salinas, CA (US)

(73) Assignee: Progeny Advanced Genetics, Salinas, CA (US)

(*) Notice: Subject to any disclaimer, the term of this patent is extended or adjusted under 35 U.S.C. 154(b) by 0 days.

(21) Appl. No.: 09/849,387

(22) Filed: May 3, 2001

(65) Prior Publication Data

US 2002/0013959 A1 Jan. 31, 2002

Related U.S. Application Data

(60) Provisional application No. 60/202,784, filed on May 9, 2000.

(51) Int. Cl.[7] ............. A01H 4/00; A01H 1/00; A01H 5/00; A01H 5/10; A01H 5/12
(52) U.S. Cl. .............. 800/305; 800/260; 800/295; 800/298; 435/410; 435/430.1
(58) Field of Search ............... 800/305, 260, 800/295, 298; 435/410, 430.1

(56) References Cited

PUBLICATIONS

Jackson et al. Nov., 1996. Iceberg Lettuce Production in California, Univ. of California Division of Agriculture and Natural Resources, Publication No. 7215.*

* cited by examiner

*Primary Examiner*—David T. Fox
*Assistant Examiner*—Francis P Moonan
(74) *Attorney, Agent, or Firm*—Morrison & Foerster LLP

(57) ABSTRACT

A new lettuce variety designated Sun Devil is described. Sun Devil is an iceberg lettuce variety exhibiting stability and uniformity. Sun Devil seed are deposited with the American Type Culture Collection and have ATCC deposit number PTA-4008.

7 Claims, 1 Drawing Sheet

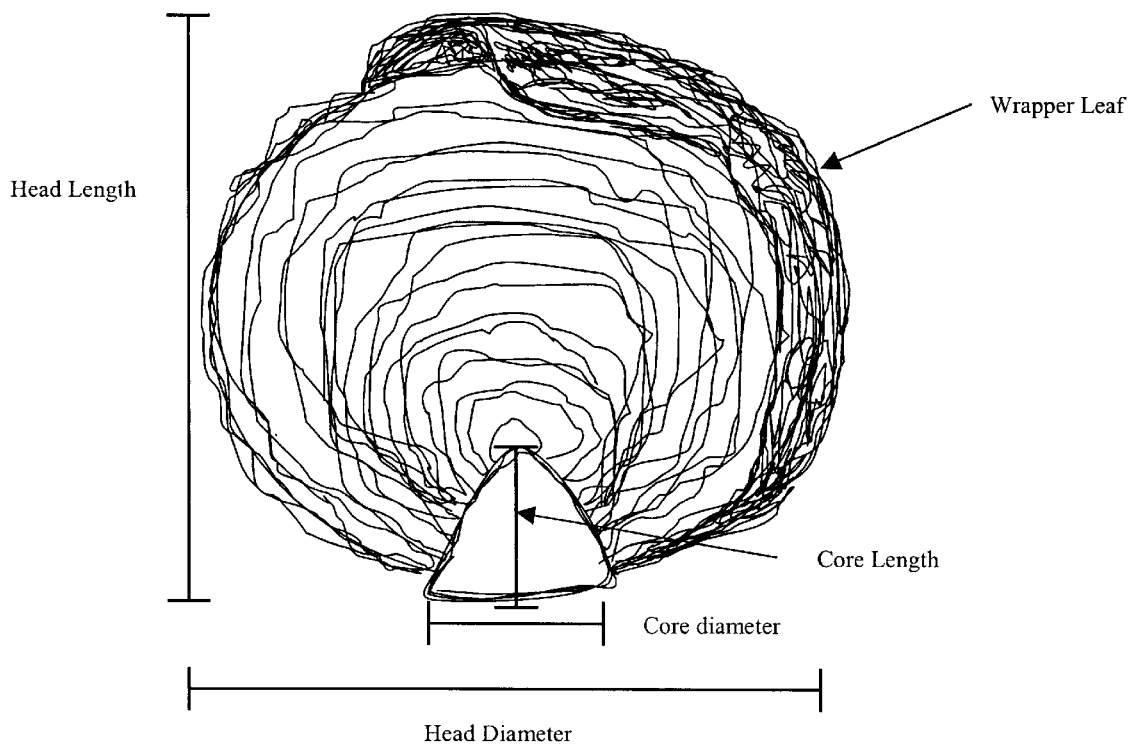

SUN DEVIL LETTUCE VARIETY

I. RELATED APPLICATION

This application claims the benefit under 35 U.S.C. §119 (e) of U.S. provisional patent application No. 60/202,784 filed May 9, 2000 which is hereby incorporated by reference in its entirety.

II. FIELD OF THE INVENTION

This invention relates to the field of plant breeding. In particular, this invention relates to a new lettuce, *Lactuca sativa*, variety, Sun Devil.

III. BACKGROUND OF THE INVENTION

Lettuce is an increasingly popular crop. Worldwide lettuce consumption continues to increase. As a result of this demand, there is a continued need for new lettuce varieties. In particular, there is a need for improved iceberg lettuce varieties that exhibit vigorous growth, increased weight and yield.

IV. SUMMARY OF THE INVENTION

In order to meet these needs, the present invention is directed to an improved iceberg lettuce variety that exhibits vigorous growth, increased weight and yield. In particular, the present invention is directed to lettuce, *Lactuca sativa*, seed designated as Sun Devil having ATCC Accession Number PTA-4008. The present invention is further directed to a lettuce, *Lactuca sativa* plant produced by growing Sun Devil lettuce seed having ATCC Accession Number PTA-4008. The present invention is further directed to a *Lactuca sativa* plant having all the physiological and morphological characteristics of a *Lactuca sativa* plant produced by growing Sun Devil lettuce seed having ATCC Accession Number PTA-4008. The present invention is further directed to an $F_1$ hybrid lettuce, *Lactuca sativa* plant having Sun Devil as a parent wherein Sun Devil is grown from Sun Devil lettuce seed having ATCC Accession Number PTA-4008.

The present invention is further directed to pollen and ovules isolated from Sun Devil lettuce plants. The present invention is further directed to tissue culture of Sun Devil lettuce plants.

The present invention is further directed to a method of selecting lettuce plants comprising a) growing Sun Devil lettuce plants wherein the Sun Devil plants are grown from lettuce seed having ATCC Accession Number PTA-4008 and b) selecting a plant from step a). The present invention is further directed to lettuce plants and seeds produced by the lettuce plants wherein the lettuce plants are isolated by the selection method of the invention.

The present invention is further directed to a method of breeding lettuce plants comprising crossing a lettuce plant with a plant grown from Sun Devil lettuce seed having ATCC Accession Number PTA-4008. The present invention is further directed to lettuce plants and seeds produced therefrom where the lettuce plant is isolated by the breeding method of the invention.

V. BRIEF DESCRIPTION OF THE DRAWING

The invention will be better understood by reference to FIG. 1 which shows a drawing of a cross-section of an iceberg lettuce head showing head length 1, head diameter 2, core diameter 3, core length 4, and a wrapper leaf 5. In the description that follows, head length, head diameter, core diameter, core length, and wrapper leaf are described without associated reference numbers, but are intended to correspond to the respective reference numbers listed above.

VI. BRIEF DESCRIPTION OF THE TABLES

The invention will be better understood by reference to the Tables in which;

Table 1 shows trial data comparing Raider and Sun Devil iceberg lettuce varieties.

Table 2 shows trial data comparing Early Sun Devil and Sun Devil iceberg lettuce varieties.

Table 3 shows trial data comparing PAG-02-23 and Sun Devil iceberg lettuce varieties.

Table 4 shows trial data comparing Van Pire and Sun Devil iceberg lettuce varieties.

Table 5 shows trial data comparing Early Sun Devil and Sun Devil iceberg lettuce varieties.

Table 6 shows trial data comparing PAG-02-23 and Sun Devil iceberg lettuce varieties.

Table 7 shows trial data comparing Van Pire and Sun Devil iceberg lettuce varieties.

Table 8 shows trial data comparing Raider and Sun Devil iceberg lettuce varieties.

Table 9 shows trial data comparing Sun Devil and Early Sun Devil iceberg Lettuce varieties.

Table 10 shows trial data comparing Sun Devil and PAG-02-23 iceberg lettuce varieties.

Table 11 shows trial data comparing Sun Devil and Van Pire iceberg Lettuce Varieties.

Table 12 shows trial data comparing Sun Devil and Raider iceberg lettuce varieities.

VII. DETAILED DESCRIPTION OF THE INVENTION

In order to more clearly understand the invention, the following definitions are provided:

Iceberg Lettuce: Iceberg lettuce, *Lactuca sativa* L. var. *capitala* L. is also known as 'crisp head' lettuce. Iceberg lettuce is a lettuce plant type that forms a firm, spherical head formed with tightly folded brittle textured foliage. Internal color ranges from white to yellow to light green. The wrapper leaves surrounding the head are wider than they are long. Leaf margins can vary by type, being entire, undulating, or frilled. Wrapper leaf color ranges from yellow green to dark green.

Core Length: Core length is the length of the internal lettuce stem. Core length is measured from the base of the cut head to the tip of the core.

Core Diameter: Core diameter is the diameter of the lettuce stem at the base of the cut head.

Head Diameter: Head diameter is the diameter of the vertically sliced lettuce plant head at its widest horizontal point, perpendicular to the stem.

Head Length: Head length is the diameter of the vertically sliced lettuce plant head as measured from the base of the cut stem to the cap leaf Average Head Diameter: Average head diamter is an average of the measured head diameter and head length of the lettuce head.

Average Head Diameter: Core Length Ratio The ratio of the average head diameter to core length is indicative of the percentage of useable product produced by the lettuce plant.

Frame Diameter: The frame diameter is a measurement of the lettuce plant diameter at its widest point. The measurement of frame diameter is from the outer most wrapper leaf tip to outer most wrapper leaf tip.

Head Weight: Head weight is the weight of the marketable lettuce plant, cut and trimmed to market specifications.

Rogueing: Rogueing is the process in seed production where undesired plants are removed from a variety. The plants are removed since they differ physically from the general desired expressed characteristics of the variety. The differences can be related to size, color, maturity, leaf texture, leaf margins, growth habit, or any other characteristic that distinguishes the plant.

Market Stage: Market stage is the stage when a lettuce plant is ready for commercial lettuce harvest. In the case of an iceberg lettuce variety, at market state the head is solid and has reached an adequate size and weight.

Taking into account these definitions, the present invention is directed to seeds of the lettuce variety Sun Devil, plants produced by growing Sun Devil lettuce seeds, plants selected from a collection of Sun Devil plants and seeds derived or produced therefrom; plants produced by crossing a lettuce plant with a Sun Devil lettuce plant and seeds derived or produced therefrom.

VIII. ORIGIN AND BREEDING HISTORY OF THE VARIETY SUN DEVIL

Sun Devil is an iceberg lettuce variety developed from a hand pollinated cross of PAG 02-23, an individual plant selection from the commercial variety Raider, available from Genecorp seed, and Van Pire also available from Genecorp Seed. The cross was made in year 1 in the San Joaquin Valley. The two parental varieties were selected for their compatibility, PAG 02-23 was the source for bolt tolerance in the fall growing conditions of the desert production locations of California and Arizona and Van Pire was selected for its size, color, and texture. The cross was made in an attempt to produce a dark green, sure heading iceberg lettuce with improved texture and size for fall plantings in Yuma, Ariz., and Huron, Calif. F1 seed was harvested.

Approximately 40 plants of the F1 seed were planted in a San Joaquin Valley production field for seed increase in year 2. The block was rogued, eliminating the self pollinating plants. The F2 seed was harvested in August year 2.

The F2 seed was evaluated in research and development plot trials in years 2 and 3. The seed was then increased in year 3 in a San Joaquin Valley production field. The block was intensely rogued at the market stage, selecting plants for improved head and frame size, bolt tolerance, and dark green color. Additional rogueing for uniformity in size and maturity was done until complete seed maturity. The remaining plants were bulk harvested producing the F3 seed in the fall of year 3. F3 seed is known as Early Sun Devil lettuce.

The F3 seed was extensively trialed throughout growing seasons of years 3 and 4 in Yuma, Arizona and the San Joaquin Valley lettuce production regions. Individual plant selections were made on the basis of increased size and later maturity. The bulk seed and seed from individual plants were increased in year 4 in the San Joaquin Valley research production. Selections were made for large head and frame size, dark green color and bolting tolerance. Further intense rogueing for size, type and maturity was done until harvest of the F4 seed. The resulting plants were noted as expressing the desired phenotypic traits.

The F4 seed was evaluated in research and development plot trials during the year 4 and 5 growing seasons in the fall plantings of Yuma, Ariz. and the San Joaquin Valley of California, where additional selections were made for improved size, color and maturity. The F4 seed was increased in year 5 in a San Joaquin Valley research production field and selectively and intensely rogued for uniformity of type, size and maturity. The F5 seed was then harvested.

During the year 5 growing season, the F5 seed was trialed in Yuma, Ariz. and the San Joaquin Valley of California. This variety was noted to exhibit the desired phenotypic traits, producing an improved large dark head and frame. The F5 seed was planted in year 6 in a San Joaquin Valley commercial production field, where it was selectively and intensely rogued for uniformity in size and maturity. The F6 seed was harvested that fall.

The F6 seed was planted in large strip trials in the year 5 and 6 growing seasons of Yuma, Ariz. The evaluation of these trials showed the variety to exhibit the desired phenotypic characteristics of improved head and frame size, dark green color, and improved texture, while being uniform, stable and without variants. The F6 seed was increased in year 7 in a San Joaquin Valley commercial production field, and selectively rogued for uniformity in size and maturity. The F7 seed was harvested.

The F6 and F7 seed of the variety Sun Devil, as evaluated in commercial trails and production, is stable and without variants.

Increased refinement of the variety Early Sun Devil was done to improve this line. Intense selection work was done to increase the size and uniformity of the Early Sun Devil plants. Refinement of the variety was successful. The current refined and distinct F7 Sun Devil is significantly more uniform, and consistently larger heading and framed, while maturing more slowly than F3 Early Sun Devil.

*Lactuca sativa* cultivar Sun Devil has the numerous distinguishing characteristics as outlined in the following summary list. In some circumstances, in the summary, Sun Devil iceberg lettuce plants were compared to Raider iceberg lettuce plants.

| A. Variety Description Information | |
|---|---|
| Plant Type: | Iceberg |
| Seed: | |
| Seed Color: | White |
| Light Dormancy: | No |
| Heat Dormancy: | Yes |
| Cotyledons: | |
| Shape of Cotyledons: | Intermediate |
| Shape of Fourth Leaf: | Spatulate |
| Length/Width Index of Fourth Leaf: | 22 |
| Apical Margin: | Finley Dentate |
| Basal Margin: | Finley Dentate |
| Undulation: | Flat |
| Green Color: | Medium |
| Anthocyanin: | Absent |
| Distribution: | None |
| Rolling: | Absent |
| Cupping: | Uncupped |
| Reflexing: | None |
| Mature Leaves: | |
| Margin: | |
| Incision Depth (Deepest penetration of the margin): | Deep |
| Indentation (Finest Division of the | Shallowly Dentate |

-continued

A. Variety Description Information

| | |
|---|---|
| Plant Type: | Iceberg |
| Margin): | |
| Undulation of the Apical Margin: | Moderate |
| Green Color: | Medium |
| Anthocyanin | |
| Distribution: | None |
| Size: | Large |
| Glossiness: | Moderate |
| Blistering: | Moderate |
| Leaf Thickness: | Intermediate |
| Trichomes: | Absent |

B. Comparison to Parent Line

| Characteristic | Sun Devil | Raider |
|---|---|---|
| Spread of Frame Leaves | 48 cm | 47 cm |
| Head Diameter (market trimmed with single cup leaf) | 16 cm | 15 cm |
| Head Shape | Round | Round |
| Head Size Class | Medium | Medium |
| Head Count per Carton | 24 | 24 |
| Head Weight | 1112 g | 1061 g |
| Head Firmness | Firm | Firm |
| Butt | Round | Round |
| Shape | Round | Round |
| Midrib | Moderately Raised | Moderately Raised |
| Core (Stem of Market-trimmed Head) | | |
| Diameter at the base of the Head | 3.7 cm | 3.4 |
| Ratio of Head Diameter/Core Diameter | 4.3 | 4.4 |
| Core Height from base of Head to Apex | 4.2 cm | 4.7 cm |
| Number of Days from First Water Date to Seed Stalk Emergence (Summer condition) | 59 | 60 |
| Bolting Class | slow | slow |
| Height of Mature Seed Stalk | 98 cm | 101 cm |
| Spread of Bolter Plant | 41 | 47 |
| Bolter Leaves | Curved | Straight |
| Margin | Dentate | Smooth/Entire |
| Color | Medium Green | Dark Green |
| Bolter Habit | | |
| Terminal Inflorescence | Present | Present |
| Lateral Shoots (above head) | Present | Present |
| Basal Side Shoots | Present | Present |
| Adaptation Regions | Huron, CA. Yuma, AZ. | Huron, CA. Yuma, AZ. |

C. Growing Season

| Season | Sun Devil | Raider |
|---|---|---|
| Spring area | NA | NA |
| Summer area | NA | NA |
| Fall area | Yuma, Az. Huron, Ca | Yuma, Az. Huron, Ca |
| Greenhouse: Not tested | | |

D. Diseases and Stress Reactions

| Disease or Stress | Sun Devil | Raider |
|---|---|---|
| Virus | | |
| Big Vein: | NA | |
| Lettuce Mosaic: | NA | |
| Cucumber Mosaic: | NA | |
| Broad Bean Wilt: | NA | |
| Turnip Mosaic: | NA | |
| Best Western Yellows: | NA | |
| Lettuce Infectious Yellows: | NA | |

E. Fungi/Bacteria

| Fungal/Bacterial | Sun Devil | Raider |
|---|---|---|
| Corky Root Rot (Pythium Root Rot): | NA | |
| Downy Mildew (Races I, IIA, III): | NA | |
| Powdery Mildew: | NA | |
| Sclerotinia Rot: | NA | |
| Bacterial Soft Rot (Pseudomonas spp. & others): Not tested | NA | |
| Botrytis (Gray Mold): | NA | |
| Other: Corky Root Rot (*Rhizomonas suberifaciens*): | NA | |

F. Insects

| Insects | Sun Devil | Raider |
|---|---|---|
| Cabbage Loopers: | NA | |
| Root Aphids: | NA | |
| Green Peach Aphid: | NA | |

G. Physiological/Stress

| Stress | Sun Devil | Raider |
|---|---|---|
| Tipburn | Intermediate | |
| Heat | Intermediate | |
| Drought | NA | |
| Cold | NA | |
| Salt | NA | |

H. Post Harvest

| Characteristic | Sun Devil | Raider |
|---|---|---|
| Pink Rib | NA | |
| Russet Spotting | NA | |
| Rusty Brown Discoloration | NA | |

-continued

| Characteristic | H. Post Harvest Sun Devil | Raider |
|---|---|---|
| Internal Rib Necrosis (Blackheart, Gray Rib, Gray Streak) | NA | |
| Brown Stain | NA | |

Breeding and Selection

The present invention is further directed to the use of Sun Devil lettuce in breeding and selection of new varieties.

A. Breeding

In lettuce breeding, lines are selected for their appropriate characteristics. For example, one line may be selected for for bolt tolerance in the fall growing conditions of the desert production locations of California and Arizona. Another line may be selected for the size, color and texture of the lettuce head. Crosses are made, for example, to produce a dark green, sure heading iceberg lettuce with improved texture, and size for fall plantings in Yuma Ariz., and Huron Calif.

To optimize crossing, it is important to note that lettuce is an obligate self-pollinating species. This means that the pollen is shed before stigma emergence, assuring 100% self-fertilization. Since each lettuce flower is an aggregate of about 10–20 individual florets (typical of the Compositae family), manual removal of the anther tubes containing the pollen may be peformed by procedures well known in the art of lettuce breeding.

In addition to manual removal of anther tubes, a modified method of misting to wash the pollen off prior to fertilization may be used to assure crossing or hybridization. About 60–90 min past sunrise, flowers to be used for crossings are selected. The basis for selection are open flowers, with the stigma emerged and the pollen visibly attached to the single stigma (about 10–20 stigma). Using 3–4 pumps of water from a regular spray bottle, the pollen are washed off with enough pressure to dislodge the pollen grains, but not enough to damage the style. Excess water is dried off with clean paper towels. About 30 min later the styles should spring back up and the two lobes of the stigma are visibly open in a "V" shape. Pollen from another variety or donor parent are then introduced by gently rubbing the stigma and style of the donor parent to the maternal parent. Tags with the pertinent information on date and pedigree are then secured to the flowers. About 2–3 weeks after pollination, seeds are harvested when the involucre have matured. The seeds are eventually sown and in the presence of markers such as leaf color or leaf margins, the selfed or maternal seedlings or plants are identified. Generally, there are no visible markers and breeders must wait until the $F_2$ generations when expected segregation patterns for the genetic character of interest can be followed. This latter situation mandates a lengthy wait to determine if hybrids are produced. Two useful references teaching the methods for out crossing lettuce are: (1) Ryder, E. J. and A. S. Johnson. 1974. Mist depollination of lettuce flowers. Hortscience 9:584; and (2) Nagata, R. T. 1992. Clip and Wash Method of Emasculation for Lettuce. Hortscience 27(8):907–908 both of which are hereby incorporated by reference in their entirety.

B. Selection

In addition to crossing, selection may be used to isolate lettuce new lettuce lines. In lettuce selection, one or more lettuce seeds are planted, the plants are grown and single plant selections are made of plants with desired characteristics. Such characteristics may include improved head and frame size, deeper or darker green leaf color, etc. Seed from the single plant selections are harvested; separated from seeds of the other plants in the field and re-planted. The plants from the selected seed are monitored to determined if they exhibit the desired characteristics from the originally selected line. Selection work is continued over multiple generations to increase the uniformity new line.

IX. DEPOSIT INFORMATION

Applicants have made available to the public without restriction a deposit of at least 2500 seeds of lettuce variety Sun Devil with the American Type Culture Collection (ATCC), Rockville, Md. 20852 on Jan. 24, 2001, which has been assigned ATCC number PTA-4008.

The deposit will be maintained in the ATCC depository, which is a public depository, for a period of 30 years, or 5 years after the most recent request, or for the effective life of the patent, whichever is longer, and will be replaced if a deposit becomes nonviable during that period.

This invention will be better understod by reference to the following non-limiting Examples.

X. EXAMPLES

Example 1: General Trialing Method

I. Set Up

The following steps illustrate the general trialing method of the invention.

1. A trial is set up to compare one or more lines. Parental lines and competing varieties are identified.

2. Primary slots are identified.

3. Necessary accession lines are located and purchased/obtained from seed dealers or growers.

4. All varieties are assigned a number to maintain integrity and anonymity.

5. Trials are set up in with all necessary varieties. Variety arrangement for trial is diagramed.

II. Planting

1. Commercial plantings are located by contacting commercial growers during the planting slot recommended for the variety.

2. A field is located during commercial planting and the necessary rows and area is marked off.

3. Varieties are planted according to a diagram, generally in 100 foot ranges.

4. All varieties are planted in same manner to mimic the planting of the commercial variety as closely as possible.

5. A trial map is drawn diagramming the trial, the trial location in the field and directions to the field.

III. Maintenance

1. All tested varieties are treated identically. Plants are watered, fertilized, and treated to control pests in the same manner as other lettuce plants in the commercial field.

2. The trial is thinned to separate the plants for optimum growth.

Example 2: Comparative Analysis

Following the procedures of Example 1, Sun Devil iceberg lettuce was compared to various other varieties. Comparative data was obtained and analyzed for different iceberg lettuce lines. Core length, core diameter, head diameter, head length, average head diameter, frame diameter and head weight as provided in the definitions section above and FIG. 1 were compared. The data are presented in Tables 1–12. Table 1 shows trial data comparing Raider and Sun Devil iceberg lettuce varieties. Table 2 shows trial data comparing Early Sun Devil and Sun Devil iceberg lettuce varieties. Table 3 shows trial data comparing PAG-02-23 and Sun Devil iceberg lettuce varieties. Table 4 shows trial data comparing Van Pire and Sun Devil iceberg lettuce varieties. Table 5 shows trial data comparing Early Sun Devil and Sun Devil iceberg lettuce varieties. Table 6 shows trial data comparing PAG-02-23 and Sun Devil iceberg lettuce varieties. Table 7 shows trial data comparing Van Pire and Sun Devil iceberg lettuce varieties. Table 8 shows trial data comparing Raider and Sun Devil iceberg lettuce varieties. Table 9 shows trial data comparing Sun Devil and Early Sun Devil iceberg Lettuce varieties. Table 10 shows trial data comparing Sun Devil and PAG-02-23 iceberg lettuce varieties. Table 11 shows trial data comparing Sun Devil and Van pire iceberg lettuce varieties. Table 12. shows trial data comparing Sun Devil and Raider iceberg lettuce varieities.

The data presented in Tables 1–12 illustrate that Sun Devil is a distinct and novel iceberg lettuce variety for clarity, the following distinctions are noted. Sun Devil as a commercial lettuce variety most closely resembles the variety Raider. It is distinguished from Raider by the following characteristics, supported statistically. (1) Sun Devil produces a larger head diameter than Raider. (2) Sun Devil produces a shorter core than Raider. (3) Sun Devil produces a larger core diameter than Raider. (4) Sun Devil is a later maturing variety than Raider. (5) Sun Devil has a larger frame diameter than Raider.

In addition to the measured characteristics, Sun Devil has a distinct leaf arcitecture and growth habit. The incision depth of the wrapper leaf margins on Sun Devil is extremely deep, while the incision depth on the Raider is moderately deep. Sun Devil grows upright, off of the beds, limiting leaf contact to the ground. This is an improvement over similar varieties as Sun Devil becomes less susceptible to bottom rot, a problem associated with contact to moist soil.

Through further selection work, the refined and improved Sun Devil is distinct from its predecessor, Early Sun Devil, supported statistically. Sun Devil is genetically and phenotypically more uniform than Early Sun Devil Sun Devil is larger heading than Early Sun Devil. Sun Devil produces a heavier head Early Sun Devil. Sun Devil is larger framed than Early Sun Devil.

In addition, Sun Devil is much truer to type than the Early Sun Devil. Sun Devil is now free of all parent type escapes and is uniform, distinct, and stable.

Sun Devil is distinct from its parent variety PAG 02-23 (a white seeded selection made from the variety Raider) by numerous characteristics, supported statistically. Sun Devil has a larger core diameter than PAG 02-23. Sun Devil has a larger frame diameter than PAG 02-23. Sun Devil has deeper incision depths in the leaf margins than PAG 02-23.

Sun Devil is distinct from its parent variety Van Pire, by the numerous characteristics supported statistically. Sun Devil produces a heavier head than Van Pire. Sun Devil is lighter in color than Van Pire. Sun Devil is smaller framed than Van Pire. Sun Devil is earlier maturing than Van Pire.

Although the foregoing invention has been described in some detail by way of illustration and examples for purposes of clarity and understanding, it will be obvious that certain modifications and alternative embodiments of the invention are contemplated which do not depart from the spirit and scope of the invention as defined by the foregoing teachings and appended claims.

TABLE 1

| Trial map #: | RSJV00051 | Location: | Tres Picos | Ranch/lot: | 35-4-4 | Date evald: | 11/3 |
|---|---|---|---|---|---|---|---|
| Wet Date: | 8/28 | Grower: | T&A | Commercial Var: | Raider | Eval by: | nd/ac/dg |

| | Core length (mm) | | Core diam (mm) | | Head diam (mm) | | Head length (mm) | |
|---|---|---|---|---|---|---|---|---|
| Sample # | Raider | SunDevil | Raider | SunDevil | Raider | SunDevil | Raider | SunDevil |
| 1 | 50.0 | 52.0 | 35.0 | 45.0 | 142.0 | 175.0 | 150.0 | 156.0 |
| 2 | 65.0 | 44.0 | 37.0 | 42.0 | 181.0 | 156.0 | 164.0 | 155.0 |
| 3 | 72.0 | 42.0 | 36.0 | 37.0 | 164.0 | 194.0 | 166.0 | 171.0 |
| 4 | 37.0 | 44.0 | 37.0 | 37.0 | 155.0 | 172.0 | 164.0 | 164.0 |
| 5 | 49.0 | 44.0 | 37.0 | 42.0 | 169.0 | 152.0 | 166.0 | 176.0 |
| 6 | 42.0 | 44.0 | 36.0 | 40.0 | 155.0 | 175.0 | 154.0 | 162.0 |
| 7 | 30.0 | 45.0 | 40.0 | 35.0 | 166.0 | 171.0 | 162.0 | 154.0 |
| 8 | 42.0 | 54.0 | 37.0 | 39.0 | 165.0 | 191.0 | 165.0 | 184.0 |
| 9 | 40.0 | 44.0 | 40.0 | 42.0 | 171.0 | 171.0 | 170.0 | 160.0 |
| 10 | 72.0 | 34.0 | 37.0 | 40.0 | 146.0 | 174.0 | 159.0 | 175.0 |
| 11 | 79.0 | 40.0 | 35.0 | 41.0 | 180.0 | 165.0 | 182.0 | 152.0 |
| 12 | 65.0 | 50.0 | 40.0 | 39.0 | 180.0 | 161.0 | 161.0 | 172.0 |
| 13 | 60.0 | 44.0 | 37.0 | 39.0 | 172.0 | 174.0 | 163.0 | 165.0 |
| 14 | 71.0 | 40.0 | 39.0 | 39.0 | 189.0 | 181.0 | 161.0 | 170.0 |
| 15 | 59.0 | 45.0 | 36.0 | 41.0 | 179.0 | 192.0 | 175.0 | 181.0 |
| 16 | 62.0 | 56.0 | 39.0 | 40.0 | 164.0 | 194.0 | 169.0 | 175.0 |
| 17 | 61.0 | 40.0 | 36.0 | 37.0 | 175.0 | 184.0 | 172.0 | 192.0 |
| 18 | 49.0 | 47.0 | 40.0 | 36.0 | 160.0 | 169.0 | 164.0 | 160.0 |
| 19 | 69.0 | 34.0 | 40.0 | 42.0 | 171.0 | 169.0 | 157.0 | 160.0 |
| 20 | 64.0 | 45.0 | 35.0 | 41.0 | 164.0 | 170.0 | 160.0 | 170.0 |
| 21 | 71.0 | 56.0 | 41.0 | 39.0 | 161.0 | 147.0 | 153.0 | 181.0 |

TABLE 1-continued

| | | | | | | | | |
|---|---|---|---|---|---|---|---|---|
| 22 | 50.0 | 42.0 | 37.0 | 42.0 | 147.0 | 170.0 | 160.0 | 172.0 |
| 23 | 55.0 | 45.0 | 40.0 | 40.0 | 160.0 | 166.0 | 164.0 | 152.0 |
| 24 | 55.0 | 50.0 | 41.0 | 39.0 | 164.0 | 181.0 | 157.0 | 156.0 |
| Average | 57.0 | 45.0 | 37.8 | 39.7 | 165.8 | 173.1 | 163.3 | 167.7 |
| Stan dev | 12.89 | 12.89 | 2.01 | 2.01 | 11.76 | 11.76 | 7.10 | 7.10 |
| T test | 1.43E−04 | | 5.51E−03 | | 4.35E−02 | | 9.68E−02 | |

| | Date Mature | Days to Maturity | Color |
|---|---|---|---|
| Raider | 11/13 | 77 | 5gy5/6 |
| SunDevil | 11/16 | 80 | 5gy4/8 |

| | Avg Head Diameter (mm) | | Avg Head Diam Core Length | | Frame Diam (cm) | | Head wt (g) | |
|---|---|---|---|---|---|---|---|---|
| Sample # | Raider | SunDevil | Raider | SunDevil | Raider | SunDevil | Raider | SunDevil |
| 1 | 146.0 | 165.5 | 2.9 | 3.2 | 49 | 44 | 630 | 916 |
| 2 | 172.5 | 155.5 | 4.7 | 3.5 | 50 | 46 | 770 | 757 |
| 3 | 165.0 | 182.5 | 4.6 | 4.3 | 46 | 46 | 766 | 840 |
| 4 | 159.5 | 169.0 | 4.3 | 3.8 | 50 | 47 | 840 | 1085 |
| 5 | 167.5 | 164.0 | 4.5 | 3.7 | 50 | 45 | 1009 | 1001 |
| 6 | 154.5 | 168.5 | 4.3 | 3.8 | 47 | 48 | 832 | 895 |
| 7 | 164.0 | 162.5 | 4.1 | 3.6 | 49 | 46 | 901 | 994 |
| 8 | 165.0 | 187.5 | 4.5 | 3.5 | 50 | 45 | 686 | 852 |
| 9 | 170.5 | 165.5 | 4.3 | 3.8 | 45 | 45 | 937 | 854 |
| 10 | 152.5 | 174.5 | 4.1 | 5.1 | 45 | 46 | 847 | 854 |
| 11 | 181.0 | 158.5 | 5.2 | 4.0 | 47 | 48 | 590 | 787 |
| 12 | 170.5 | 166.5 | 4.3 | 3.3 | 44 | 46 | 774 | 804 |
| 13 | 167.5 | 169.5 | 4.5 | 3.9 | 48 | 49 | 718 | 1098 |
| 14 | 175.5 | 175.5 | 4.5 | 4.4 | 46 | 46 | 672 | 870 |
| 15 | 177.0 | 186.5 | 4.9 | 4.1 | 48 | 45 | 798 | 903 |
| 16 | 166.5 | 184.5 | 4.3 | 3.3 | 44 | 47 | 691 | 773 |
| 17 | 173.5 | 189.0 | 4.8 | 4.7 | 45 | 46 | 612 | 781 |
| 18 | 162.0 | 164.5 | 4.1 | 3.5 | 44 | 46 | 894 | 846 |
| 19 | 164.0 | 164.5 | 4.1 | 4.8 | 45 | 49 | 798 | 1053 |
| 20 | 162.0 | 170.0 | 4.6 | 3.8 | 44 | 51 | 867 | 891 |
| 21 | 157.0 | 164.0 | 3.8 | 2.9 | 46 | 47 | 792 | 904 |
| 22 | 153.5 | 171.0 | 4.1 | 4.1 | 44 | 49 | 706 | 1137 |
| 23 | 162.0 | 159.0 | 4.1 | 3.5 | 42 | 44 | 669 | 859 |
| 24 | 160.5 | 193.5 | 3.9 | 3.3 | 49 | 49 | 833 | 726 |
| Average | 164.5 | 170.4 | 4.3 | 3.8 | 46.5 | 46.7 | 776.3 | 895.0 |
| Stan dev | 8.35 | 8.35 | 0.44 | 0.44 | 2.41 | 2.41 | 107.05 | 107.05 |
| T test | 2.74E−02 | | 1.85E−03 | | 8.39E−01 | | 5.00E−04 | |

TABLE 2

| Trial map #: | RSJV00051 | Location: | Tres Picos | Ranch/lot: | 35-4-4 | Date evald: | 11/3 |
|---|---|---|---|---|---|---|---|
| Wet Date: | 8/28 | Grower: | T&A | Commercial Var: | Raider | Eval by: | nd/ac/dg |

| | Core length (mm) | | Core diam (mm) | | Head diam (mm) | | Head length (mm) | |
|---|---|---|---|---|---|---|---|---|
| Sample # | EarlySun Devil | SunDevil | EarlySun Devil | SunDevil | EarlySun Devil | SunDevil | EarlySun Devil | SunDevil |
| 1 | 40.0 | 52.0 | 36.0 | 45.0 | 155.0 | 175.0 | 160.0 | 156.0 |
| 2 | 42.0 | 44.0 | 37.0 | 42.0 | 150.0 | 156.0 | 145.0 | 155.0 |
| 3 | 45.0 | 42.0 | 35.0 | 37.0 | 147.0 | 194.0 | 155.0 | 171.0 |
| 4 | 42.0 | 44.0 | 35.0 | 37.0 | 179.0 | 172.0 | 160.0 | 164.0 |
| 5 | 45.0 | 44.0 | 39.0 | 42.0 | 140.0 | 152.0 | 170.0 | 165.0 |
| 6 | 32.0 | 44.0 | 40.0 | 40.0 | 165.0 | 175.0 | 156.0 | 162.0 |
| 7 | 30.0 | 45.0 | 36.0 | 35.0 | 150.0 | 171.0 | 154.0 | 154.0 |
| 8 | 47.0 | 54.0 | 35.0 | 39.0 | 139.0 | 191.0 | 155.0 | 184.0 |
| 9 | 45.0 | 44.0 | 42.0 | 42.0 | 160.0 | 171.0 | 162.0 | 160.0 |
| 10 | 50.0 | 34.0 | 37.0 | 40.0 | 139.0 | 174.0 | 165.0 | 156.0 |
| 11 | 46.0 | 40.0 | 35.0 | 41.0 | 146.0 | 165.0 | 160.0 | 152.0 |
| 12 | 39.0 | 50.0 | 36.0 | 39.0 | 165.0 | 161.0 | 169.0 | 172.0 |
| 13 | 35.0 | 44.0 | 37.0 | 39.0 | 179.0 | 174.0 | 154.0 | 165.0 |
| 14 | 40.0 | 40.0 | 40.0 | 39.0 | 176.0 | 181.0 | 148.0 | 170.0 |
| 15 | 57.0 | 45.0 | 35.0 | 41.0 | 159.0 | 192.0 | 172.0 | 181.0 |
| 16 | 42.0 | 56.0 | 39.0 | 40.0 | 164.0 | 194.0 | 165.0 | 175.0 |
| 17 | 42.0 | 40.0 | 36.0 | 37.0 | 136.0 | 184.0 | 154.0 | 192.0 |
| 18 | 35.0 | 47.0 | 40.0 | 36.0 | 160.0 | 169.0 | 157.0 | 160.0 |
| 19 | 42.0 | 34.0 | 40.0 | 42.0 | 159.0 | 169.0 | 159.0 | 160.0 |
| 20 | 35.0 | 45.0 | 37.0 | 41.0 | 155.0 | 170.0 | 150.0 | 170.0 |
| 21 | 37.0 | 56.0 | 35.0 | 39.0 | 139.0 | 147.0 | 151.0 | 181.0 |
| 22 | 39.0 | 42.0 | 39.0 | 42.0 | 149.0 | 170.0 | 151.0 | 172.0 |

TABLE 2-continued

| | | | | | | | | |
|---|---|---|---|---|---|---|---|---|
| 23 | 41.0 | 45.0 | 39.0 | 40.0 | 189.0 | 166.0 | 186.0 | 176.0 |
| 24 | 47.0 | 50.0 | 39.0 | 38.0 | 164.0 | 181.0 | 165.0 | 166.0 |
| Average | 41.5 | 45.0 | 37.4 | 39.7 | 156.8 | 173.1 | 159.3 | 167.5 |
| Stan dev | 5.96 | 5.77 | 2.08 | 2.33 | 14.29 | 12.42 | 9.05 | 10.43 |
| T test | 3.99E−02 | | 8.00E−04 | | 1.19E−04 | | 5.52E−03 | |

| | Date Mature | Days to Maturity | Color |
|---|---|---|---|
| EarlySun Devil | 11/6 | 70 | 5gy4/6 |
| SunDevil | 11/6 | −295 | 5gy4/8 |

| | Avg Head Diameter (mm) | | Avg Head Diam Core Length | | Frame Diam (cm) | | Head wt (g) | |
|---|---|---|---|---|---|---|---|---|
| Sample # | EarlySun Devil | SunDevil | EarlySun Devil | SunDevil | EarlySun Devil | SunDevil | EarlySun Devil | SunDevil |
| 1 | 157.5 | 165.5 | 3.9 | 32 | 49 | 44 | 578 | 916 |
| 2 | 147.5 | 155.5 | 3.5 | 3.5 | 44 | 46 | 785 | 757 |
| 3 | 151.0 | 182.5 | 3.4 | 4.3 | 45 | 46 | 928 | 840 |
| 4 | 169.5 | 169.0 | 4.0 | 3.8 | 45 | 47 | 793 | 1085 |
| 5 | 155.0 | 159.0 | 3.4 | 3.6 | 49 | 45 | 861 | 1001 |
| 6 | 160.5 | 168.5 | 5.0 | 3.8 | 43 | 48 | 725 | 895 |
| 7 | 152.0 | 162.0 | 5.1 | 3.7 | 46 | 46 | 845 | 994 |
| 8 | 147.0 | 187.5 | 3.1 | 4.2 | 38 | 45 | 611 | 852 |
| 9 | 161.0 | 165.5 | 3.6 | 3.1 | 46 | 45 | 931 | 854 |
| 10 | 152.0 | 165.0 | 3.0 | 3.8 | 44 | 46 | 814 | 854 |
| 11 | 153.0 | 158.5 | 3.3 | 4.7 | 42 | 48 | 509 | 787 |
| 12 | 167.0 | 166.5 | 4.3 | 4.2 | 40 | 46 | 559 | 804 |
| 13 | 166.5 | 169.5 | 4.8 | 3.4 | 46 | 49 | 882 | 1098 |
| 14 | 162.0 | 175.5 | 4.1 | 4.0 | 46 | 46 | 743 | 870 |
| 15 | 165.5 | 186.5 | 2.9 | 4.7 | 44 | 45 | 898 | 903 |
| 16 | 164.5 | 184.5 | 3.9 | 4.1 | 40 | 47 | 801 | 773 |
| 17 | 145.0 | 189.0 | 3.5 | 4.7 | 40 | 46 | 792 | 781 |
| 18 | 158.5 | 164.5 | 4.5 | 3.5 | 48 | 46 | 797 | 846 |
| 19 | 158.5 | 164.5 | 3.8 | 4.8 | 46 | 49 | 876 | 1053 |
| 20 | 152.5 | 170.0 | 4.4 | 3.8 | 46 | 51 | 862 | 891 |
| 21 | 145.0 | 164.0 | 3.9 | 2.9 | 45 | 47 | 831 | 904 |
| 22 | 150.0 | 171.0 | 3.8 | 4.1 | 39 | 49 | 687 | 1137 |
| 23 | 187.5 | 171.0 | 4.6 | 3.8 | 40 | 44 | 951 | 859 |
| 24 | 164.5 | 173.5 | 3.5 | 3.5 | 41 | 49 | 875 | 726 |
| Average | 159.0 | 170.3 | 3.9 | 3.9 | 43.8 | 46.7 | 788.9 | 895.0 |
| Stan dev | 9.66 | 9.38 | 0.60 | 0.52 | 3.17 | 1.79 | 121.88 | 112.38 |
| T test | 5.43E−05 | | 9.47E−01 | | 4.06E−04 | | 2.99E−03 | |

TABLE 3

| Trial map #: | RSJV00051 | Location: | Tres Picos | Ranch/lot: | 35-4-4 | Date evald: | 11/3 |
|---|---|---|---|---|---|---|---|
| Wet Date: | 8/28 | Grower: | T&A | Commercial Var: | Raider | Eval by: | nd/ac/dg |

| | Core length (mm) | | Core diam (mm) | | Head diam (mm) | | Head length (mm) | |
|---|---|---|---|---|---|---|---|---|
| Sample # | PAG02-23 | SunDevil | PAG02-23 | SunDevil | PAG02-03 | SunDevil | PAG02-23 | SunDevil |
| 1 | 44.0 | 52.0 | 39.0 | 45.0 | 165.0 | 175.0 | 139.0 | 156.0 |
| 2 | 65.0 | 44.0 | 32.0 | 42.0 | 160.0 | 156.0 | 139.0 | 155.0 |
| 3 | 47.0 | 42.0 | 39.0 | 37.0 | 155.0 | 194.0 | 161.0 | 171.0 |
| 4 | 57.0 | 44.0 | 35.0 | 37.0 | 184.0 | 172.0 | 166.0 | 164.0 |
| 5 | 42.0 | 44.0 | 35.0 | 42.0 | 172.0 | 152.0 | 164.0 | 176.0 |
| 6 | 42.0 | 44.0 | 36.0 | 40.0 | 155.0 | 175.0 | 154.0 | 162.0 |
| 7 | 42.0 | 45.0 | 37.0 | 35.0 | 174.0 | 171.0 | 150.0 | 154.0 |
| 8 | 47.0 | 54.0 | 35.0 | 39.0 | 161.0 | 191.0 | 169.0 | 184.0 |
| 9 | 59.0 | 44.0 | 40.0 | 42.0 | 161.0 | 171.0 | 162.0 | 160.0 |
| 10 | 33.0 | 34.0 | 32.0 | 40.0 | 135.0 | 174.0 | 141.0 | 175.0 |
| 11 | 42.0 | 40.0 | 39.0 | 41.0 | 156.0 | 165.0 | 151.0 | 152.0 |
| 12 | 52.0 | 50.0 | 40.0 | 39.0 | 161.0 | 161.0 | 149.0 | 172.0 |
| 13 | 40.0 | 44.0 | 36.0 | 39.0 | 155.0 | 174.0 | 173.0 | 165.0 |
| 14 | 47.0 | 40.0 | 37.0 | 38.0 | 160.0 | 181.0 | 157.0 | 170.0 |
| 15 | 45.0 | 45.0 | 34.0 | 41.0 | 161.0 | 192.0 | 160.0 | 181.0 |
| 16 | 40.0 | 56.0 | 41.0 | 40.0 | 162.0 | 194.0 | 149.0 | 175.0 |
| 17 | 42.0 | 40.0 | 39.0 | 37.0 | 156.0 | 184.0 | 155.0 | 192.0 |
| 18 | 33.0 | 47.0 | 37.0 | 36.0 | 174.0 | 169.0 | 146.0 | 160.0 |
| 19 | 46.0 | 34.0 | 39.0 | 42.0 | 162.0 | 169.0 | 155.0 | 160.0 |
| 20 | 35.0 | 45.0 | 40.0 | 41.0 | 172.0 | 170.0 | 166.0 | 170.0 |
| 21 | 50.0 | 56.0 | 40.0 | 39.0 | 169.0 | 147.0 | 155.0 | 181.0 |
| 22 | 66.0 | 42.0 | 35.0 | 42.0 | 150.0 | 170.0 | 156.0 | 172.0 |

TABLE 3-continued

| | | | | | | | | |
|---|---|---|---|---|---|---|---|---|
| 23 | 45.0 | 45.0 | 40.0 | 40.0 | 146.0 | 166.0 | 157.0 | 152.0 |
| 24 | 47.0 | 50.0 | 39.0 | 39.0 | 120.0 | 181.0 | 161.0 | 169.0 |
| Average | 46.2 | 45.0 | 37.3 | 39.7 | 161.5 | 173.1 | 155.6 | 167.7 |
| Stan dev | 8.66 | 5.77 | 2.59 | 2.33 | 10.32 | 12.42 | 9.07 | 10.75 |
| T test | 5.99E−01 | | 1.43E−03 | | 1.00E−03 | | 1.18E−04 | |

| | Date Mature | Days to Maturity | Color |
|---|---|---|---|
| PAG02-23 | 11/4 | 68 | 5gy5/6 |
| SunDevil | 11/6 | 70 | 5gy4/8 |

| | Avg Head Diameter (mm) | | Avg Head Diam Core Length | | Frame Diam (cm) | | Head wt (g) | |
|---|---|---|---|---|---|---|---|---|
| Sample # | PAG02-23 | SunDevil | PAG02-23 | SunDevil | PAG02-23 | SunDevil | PAG02-23 | SunDevil |
| 1 | 152.0 | 165.5 | 3.5 | 3.2 | 44 | 44 | 864 | 916 |
| 2 | 149.5 | 155.5 | 2.3 | 3.5 | 44 | 46 | 600 | 757 |
| 3 | 159.0 | 182.5 | 3.4 | 4.3 | 44 | 46 | 922 | 840 |
| 4 | 175.0 | 169.0 | 3.1 | 3.8 | 41 | 47 | 1013 | 1085 |
| 5 | 169.0 | 164.0 | 4.0 | 3.7 | 43 | 45 | 694 | 1001 |
| 6 | 154.5 | 168.5 | 3.7 | 3.8 | 46 | 48 | 987 | 895 |
| 7 | 162.0 | 162.5 | 3.9 | 3.7 | 40 | 46 | 937 | 994 |
| 8 | 165.0 | 187.5 | 3.5 | 4.2 | 46 | 45 | 814 | 852 |
| 9 | 161.5 | 165.5 | 2.7 | 3.1 | 45 | 45 | 724 | 854 |
| 10 | 139.0 | 174.5 | 4.2 | 4.0 | 49 | 46 | 904 | 854 |
| 11 | 153.5 | 158.5 | 3.7 | 4.7 | 49 | 48 | 894 | 787 |
| 12 | 155.0 | 166.5 | 3.0 | 4.2 | 42 | 46 | 773 | 804 |
| 13 | 164.0 | 169.5 | 4.1 | 3.4 | 40 | 49 | 569 | 1098 |
| 14 | 158.5 | 175.5 | 3.4 | 4.0 | 42 | 46 | 780 | 870 |
| 15 | 160.5 | 186.5 | 3.6 | 4.7 | 41 | 45 | 968 | 903 |
| 16 | 155.5 | 184.5 | 3.9 | 4.1 | 40 | 47 | 751 | 773 |
| 17 | 155.5 | 189.0 | 3.7 | 4.7 | 40 | 46 | 803 | 781 |
| 18 | 160.0 | 164.5 | 4.8 | 3.5 | 43 | 46 | 867 | 846 |
| 19 | 158.5 | 164.5 | 3.4 | 4.8 | 45 | 49 | 830 | 1053 |
| 20 | 169.0 | 170.0 | 4.8 | 3.8 | 43 | 51 | 731 | 891 |
| 21 | 162.0 | 164.0 | 3.2 | 2.9 | 42 | 47 | 822 | 904 |
| 22 | 153.0 | 171.0 | 2.3 | 4.1 | 42 | 49 | 692 | 1137 |
| 23 | 151.5 | 159.0 | 3.4 | 3.5 | 45 | 44 | 695 | 859 |
| 24 | 165.5 | 173.5 | 3.5 | 3.5 | 46 | 49 | 796 | 726 |
| Average | 158.6 | 170.4 | 3.5 | 3.9 | 43.4 | 46.7 | 809.6 | 895.0 |
| Stan dev | 7.60 | 9.42 | 0.63 | 0.52 | 2.62 | 1.79 | 116.32 | 112.38 |
| T test | 1.77E−05 | | 4.72E−02 | | 8.16E−06 | | 129E−02 | |

TABLE 4

| Trial map #: | RSJV00051 | Location: | Tres Picos | Ranch/lot: | 35-4-4 | Date evald: | 11/3 |
|---|---|---|---|---|---|---|---|
| Wet Date: | 8/28 | Grower: | T&A | Commercial Var: | Raider | Eval by: | nd/ac/dg |

| | Core length (mm) | | Core diam (mm) | | Head diam (mm) | | Head length (mm) | |
|---|---|---|---|---|---|---|---|---|
| Sample # | VanPire | SunDevil | VanPire | SunDevil | VanPire | SunDevil | VanPire | SunDevil |
| 1 | 50.0 | 50.0 | 34.0 | 35.0 | 162.0 | 142.0 | 145.0 | 150.0 |
| 2 | 75.0 | 65.0 | 35.0 | 37.0 | 172.0 | 181.0 | 160.0 | 164.0 |
| 3 | 52.0 | 72.0 | 35.0 | 36.0 | 187.0 | 164.0 | 152.0 | 166.0 |
| 4 | 55.0 | 37.0 | 37.0 | 37.0 | 173.0 | 155.0 | 162.0 | 164.0 |
| 5 | 50.0 | 48.0 | 35.0 | 37.0 | 154.0 | 169.0 | 147.0 | 166.0 |
| 6 | 45.0 | 42.0 | 40.0 | 36.0 | 144.0 | 155.0 | 151.0 | 154.0 |
| 7 | 45.0 | 30.0 | 37.0 | 40.0 | 164.0 | 166.0 | 155.0 | 162.0 |
| 8 | 42.0 | 42.0 | 37.0 | 37.0 | 191.0 | 165.0 | 154.0 | 165.0 |
| 9 | 32.0 | 40.0 | 35.0 | 40.0 | 165.0 | 171.0 | 154.0 | 170.0 |
| 10 | 50.0 | 72.0 | 35.0 | 37.0 | 156.0 | 146.0 | 159.0 | 159.0 |
| 11 | 47.0 | 79.0 | 36.0 | 35.0 | 161.0 | 180.0 | 156.0 | 182.0 |
| 12 | 52.0 | 65.0 | 40.0 | 40.0 | 154.0 | 180.0 | 155.0 | 161.0 |
| 13 | 60.0 | 60.0 | 36.0 | 37.0 | 159.0 | 172.0 | 154.0 | 163.0 |
| 14 | 64.0 | 71.0 | 36.0 | 39.0 | 169.0 | 189.0 | 155.0 | 161.0 |
| 15 | 32.0 | 59.0 | 34.0 | 36.0 | 148.0 | 179.0 | 149.0 | 175.0 |
| 16 | 36.0 | 62.0 | 40.0 | 39.0 | 180.0 | 164.0 | 146.0 | 169.0 |
| 17 | 60.0 | 61.0 | 40.0 | 36.0 | 182.0 | 175.0 | 149.0 | 172.0 |
| 18 | 40.0 | 49.0 | 32.0 | 40.0 | 171.0 | 160.0 | 160.0 | 164.0 |
| 19 | 55.0 | 69.0 | 35.0 | 40.0 | 190.0 | 171.0 | 157.0 | 157.0 |
| 20 | 52.0 | 64.0 | 37.0 | 35.0 | 171.0 | 164.0 | 150.0 | 160.0 |
| 21 | 51.0 | 71.0 | 35.0 | 41.0 | 191.0 | 161.0 | 154.0 | 153.0 |
| 22 | 54.0 | 50.0 | 32.0 | 37.0 | 172.0 | 147.0 | 150.0 | 160.0 |
| 23 | 51.0 | 55.0 | 35.0 | 40.0 | 166.0 | 160.0 | 150.0 | 164.0 |
| 24 | 50.0 | 55.0 | 41.0 | 41.0 | 144.0 | 164.0 | 150.0 | 157.0 |

TABLE 4-continued

| | | | | | | | | |
|---|---|---|---|---|---|---|---|---|
| Average | 50.0 | 57.0 | 36.2 | 37.8 | 167.8 | 165.8 | 153.1 | 163.3 |
| Stan dev | 9.71 | 12.89 | 2.47 | 2.01 | 14.14 | 11.76 | 4.56 | 7.10 |
| T test | 3.90E−02 | | 1.61E−02 | | 6.12E−01 | | | |

| | Date Mature | Days to Maturity | Color |
|---|---|---|---|
| VanPire | 11/8 | 72 | 5gy4/4 |
| SunDevil | 11/6 | 70 | 5gy4/8 |

| | Avg Head Diameter (mm) | | Avg Head Diam Core Length | | Frame Diam (cm) | | Head wt (g) | |
|---|---|---|---|---|---|---|---|---|
| Sample # | VanPire | SunDevil | VanPire | SunDevil | VanPire | SunDevil | VanPire | SunDevil |
| 1 | 153.5 | 146.0 | 3.1 | 2.9 | 50 | 49 | 656 | 916 |
| 2 | 166.0 | 172.5 | 2.2 | 2.7 | 52 | 50 | 777 | 757 |
| 3 | 169.5 | 165.0 | 3.3 | 2.3 | 55 | 46 | 735 | 840 |
| 4 | 167.5 | 159.5 | 3.0 | 4.3 | 50 | 50 | 693 | 1085 |
| 5 | 150.5 | 167.5 | 3.0 | 4.5 | 52 | 50 | 866 | 1001 |
| 6 | 147.5 | 154.5 | 3.3 | 3.2 | 56 | 47 | 762 | 895 |
| 7 | 159.5 | 164.0 | 3.5 | 3.9 | 49 | 49 | 1082 | 994 |
| 8 | 172.5 | 165.0 | 4.1 | 5.5 | 49 | 50 | 735 | 852 |
| 9 | 159.5 | 170.5 | 5.0 | 4.1 | 52 | 45 | 811 | 854 |
| 10 | 157.5 | 152.5 | 3.2 | 3.8 | 46 | 45 | 741 | 854 |
| 11 | 158.5 | 181.0 | 3.4 | 2.5 | 49 | 47 | 842 | 787 |
| 12 | 154.5 | 170.5 | 3.0 | 2.2 | 50 | 44 | 930 | 804 |
| 13 | 156.5 | 167.5 | 2.6 | 2.6 | 48 | 48 | 853 | 1098 |
| 14 | 162.0 | 175.0 | 2.5 | 2.9 | 49 | 46 | 767 | 870 |
| 15 | 148.5 | 177.0 | 4.6 | 2.5 | 49 | 48 | 1018 | 903 |
| 16 | 163.0 | 166.5 | 4.5 | 2.8 | 48 | 44 | 673 | 773 |
| 17 | 165.5 | 173.5 | 2.8 | 2.8 | 47 | 45 | 789 | 781 |
| 18 | 165.5 | 162.0 | 4.1 | 3.3 | 50 | 44 | 550 | 846 |
| 19 | 173.5 | 164.0 | 3.2 | 2.4 | 46 | 45 | 678 | 1053 |
| 20 | 160.5 | 162.0 | 3.1 | 2.5 | 48 | 44 | 736 | 891 |
| 21 | 172.5 | 157.0 | 3.4 | 2.2 | 49 | 46 | 625 | 904 |
| 22 | 161.0 | 153.5 | 3.0 | 3.1 | 47 | 44 | 825 | 1137 |
| 23 | 158.0 | 162.0 | 3.1 | 2.9 | 47 | 42 | 670 | 859 |
| 24 | 147.0 | 160.5 | 2.9 | 2.9 | 49 | 49 | 764 | 726 |
| Average | 160.4 | 164.5 | 3.3 | 3.1 | 49.5 | 46.5 | 774.1 | 895.0 |
| Stan dev | 7.78 | 8.35 | 0.68 | 0.83 | 2.50 | 2.41 | 120.01 | 112.38 |
| T test | 8.32E−02 | | 3.52E−01 | | 1.61E−04 | | 7.69E−04 | |

TABLE 5

| Trial map #: | YM00025 | Location: | Yuma Valley | Ranch/lot: | Huber 5 | Date evald: | 12/6 |
|---|---|---|---|---|---|---|---|
| Wet Date: | 9/20 | Grower: | Mission Ranches | Commercial Var: | Raider | Eval by: | dg/jt |

| | Core length (mm) | | Core diam (mm) | | Head diam (mm) | | Head length (mm) | |
|---|---|---|---|---|---|---|---|---|
| Sample # | EarlySun Devil | SunDevil | EarlySun Devil | SunDevil | EarlySun Devil | SunDevil | EarlySun Devil | SunDevil |
| 1 | 27.0 | 25.0 | 35.0 | 30.0 | 117.0 | 134.0 | 140.0 | 140.0 |
| 2 | 29.0 | 15.0 | 40.0 | 33.0 | 156.0 | 175.0 | 189.0 | 165.0 |
| 3 | 25.0 | 20.0 | 28.0 | 31.0 | 189.0 | 129.0 | 196.0 | 151.0 |
| 4 | 27.0 | 22.0 | 33.0 | 30.0 | 130.0 | 165.0 | 155.0 | 156.0 |
| 5 | 25.0 | 27.0 | 41.0 | 34.0 | 150.0 | 162.0 | 116.0 | 175.0 |
| 6 | 25.0 | 20.0 | 46.0 | 30.0 | 151.0 | 152.0 | 160.0 | 170.0 |
| 7 | 30.0 | 28.0 | 35.0 | 36.0 | 113.0 | 144.0 | 134.0 | 151.0 |
| 8 | 20.0 | 20.0 | 30.0 | 32.0 | 150.0 | 156.0 | 130.0 | 170.0 |
| 9 | 22.0 | 22.0 | 36.0 | 30.0 | 170.0 | 160.0 | 160.0 | 150.0 |
| 10 | 29.0 | 20.0 | 35.0 | 30.0 | 171.0 | 162.0 | 152.0 | 144.0 |
| 11 | 20.0 | 15.0 | 35.0 | 34.0 | 149.0 | 151.0 | 122.0 | 139.0 |
| 12 | 25.0 | 19.0 | 35.0 | 32.0 | 142.0 | 172.0 | 140.0 | 130.0 |
| 13 | 26.0 | 30.0 | 34.0 | 32.0 | 135.0 | 162.0 | 141.0 | 155.0 |
| 14 | 17.0 | 21.0 | 34.0 | 31.0 | 140.0 | 139.0 | 139.0 | 139.0 |
| 15 | 15.0 | 30.0 | 36.0 | 35.0 | 162.0 | 149.0 | 138.0 | 145.0 |
| 16 | 25.0 | 25.0 | 30.0 | 32.0 | 159.0 | 146.0 | 155.0 | 134.0 |
| 17 | 29.0 | 20.0 | 35.0 | 34.0 | 156.0 | 172.0 | 158.0 | 130.0 |
| 18 | 20.0 | 21.0 | 30.0 | 31.0 | 130.0 | 172.0 | 135.0 | 141.0 |
| 19 | 26.0 | 25.0 | 39.0 | 32.0 | 130.0 | 165.0 | 131.0 | 149.0 |
| 20 | 27.0 | 18.0 | 35.0 | 32.0 | 155.0 | 156.0 | 153.0 | 139.0 |
| 21 | 20.0 | 20.0 | 32.0 | 31.0 | 155.0 | 156.0 | 179.0 | 139.0 |
| 22 | 27.0 | 21.0 | 35.0 | 34.0 | 125.0 | 165.0 | 126.0 | 169.0 |
| 23 | 27.0 | 31.0 | 36.0 | 35.0 | 102.0 | 180.0 | 180.0 | 156.0 |

TABLE 5-continued

| | | | | | | | | |
|---|---|---|---|---|---|---|---|---|
| 24 | 22.0 | 20.0 | 28.0 | 32.0 | 125.0 | 166.0 | 131.0 | 125.0 |
| Average | 24.4 | 22.3 | 34.7 | 32.2 | 144.3 | 157.9 | 148.3 | 148.4 |
| Stan dev | 4.00 | 4.42 | 4.10 | 1.79 | 20.34 | 13.05 | 21.17 | 13.92 |
| T test | 9.35E−02 | | 8.81E−03 | | 8.06E−03 | | 9.87E−01 | |

| | Date Mature | Days to Maturity | Color |
|---|---|---|---|
| EarlySun Devil | 12/12 | 83 | 5gy4/6 |
| SunDevil | 12/12 | 83 | 5gy4/6 |

| | Avg Head Diameter (mm) | | Avg Head Diam Core Length | | Frame Diam (cm) | | Head wt (g) | |
|---|---|---|---|---|---|---|---|---|
| Sample # | EarlySun Devil | SunDevil | EarlySun Devil | SunDevil | EarlySun Devil | SunDevil | EarlySun Devil | SunDevil |
| 1 | 128.5 | 137.0 | 4.8 | 5.5 | 48 | 44 | 472 | 665 |
| 2 | 172.5 | 170.0 | 5.9 | 11.3 | 39 | 44 | 948 | 709 |
| 3 | 192.5 | 140.0 | 7.7 | 7.0 | 43 | 45 | 546 | 652 |
| 4 | 142.5 | 160.5 | 5.3 | 7.3 | 47 | 46 | 582 | 635 |
| 5 | 133.0 | 168.5 | 5.3 | 7.7 | 48 | 48 | 658 | 610 |
| 6 | 155.5 | 161.0 | 6.2 | 6.0 | 48 | 49 | 468 | 685 |
| 7 | 123.5 | 147.5 | 4.1 | 7.4 | 42 | 45 | 689 | 627 |
| 8 | 140.0 | 163.0 | 7.0 | 5.8 | 44 | 46 | 540 | 611 |
| 9 | 165.0 | 155.0 | 7.5 | 7.8 | 44 | 48 | 692 | 646 |
| 10 | 161.5 | 153.0 | 5.6 | 7.0 | 43 | 45 | 562 | 597 |
| 11 | 135.5 | 145.0 | 6.8 | 7.3 | 45 | 44 | 781 | 903 |
| 12 | 141.0 | 151.0 | 5.6 | 10.1 | 48 | 46 | 526 | 674 |
| 13 | 138.0 | 158.5 | 5.3 | 8.3 | 52 | 49 | 584 | 760 |
| 14 | 139.5 | 139.0 | 8.2 | 4.6 | 40 | 42 | 580 | 610 |
| 15 | 150.0 | 147.0 | 10.0 | 7.0 | 44 | 43 | 630 | 739 |
| 16 | 157.0 | 140.0 | 6.3 | 4.7 | 42 | 45 | 420 | 676 |
| 17 | 157.0 | 151.0 | 5.4 | 7.6 | 44 | 46 | 635 | 667 |
| 18 | 132.5 | 156.5 | 6.6 | 7.5 | 47 | 49 | 613 | 628 |
| 19 | 130.5 | 157.0 | 5.0 | 6.3 | 45 | 49 | 699 | 674 |
| 20 | 154.0 | 147.5 | 5.7 | 8.2 | 41 | 49 | 750 | 694 |
| 21 | 167.0 | 147.5 | 8.4 | 7.4 | 44 | 50 | 675 | 663 |
| 22 | 125.5 | 167.0 | 4.6 | 8.0 | 42 | 51 | 389 | 596 |
| 23 | 141.0 | 168.0 | 5.2 | 5.4 | 40 | 50 | 796 | 652 |
| 24 | 128.0 | 145.5 | 5.8 | 7.3 | 49 | 49 | 721 | 638 |
| Average | 146.3 | 153.2 | 6.2 | 7.2 | 44.5 | 46.8 | 606.5 | 667.1 |
| Stan dev | 17.17 | 9.95 | 1.38 | 1.51 | 3.27 | 2.52 | 140.53 | 65.27 |
| T test | 9.64E−02 | | 2.23E−02 | | 1.19E−02 | | 6.15E−02 | |

TABLE 6

| Trial map #: | YM00025 | Location: | Yuma Valley | Ranch/lot: | Huber 5 | Date evald: | 12/6 |
|---|---|---|---|---|---|---|---|
| Wet Date: | 9/20 | Grower: | Mission Ranches | Commercial Var: | Raider | Eval by: | dg/jt |

| | Core length (mm) | | Core diam (mm) | | Head diam (mm) | | Head length (mm) | |
|---|---|---|---|---|---|---|---|---|
| Sample # | PAG02-23 | SunDevil | PAG02-23 | SunDevil | PAG02-23 | SunDevil | PAG02-23 | SunDevil |
| 1 | 17.0 | 25.0 | 34.0 | 30.0 | 146.0 | 134.0 | 150.0 | 140.0 |
| 2 | 15.0 | 15.0 | 30.0 | 33.0 | 150.0 | 175.0 | 131.0 | 165.0 |
| 3 | 15.0 | 20.0 | 34.0 | 31.0 | 130.0 | 129.0 | 155.0 | 151.0 |
| 4 | 20.0 | 22.0 | 33.0 | 30.0 | 126.0 | 165.0 | 121.0 | 156.0 |
| 5 | 15.0 | 27.0 | 32.0 | 34.0 | 128.0 | 162.0 | 125.0 | 175.0 |
| 6 | 16.0 | 20.0 | 33.0 | 30.0 | 120.0 | 152.0 | 144.0 | 170.0 |
| 7 | 25.0 | 28.0 | 32.0 | 36.0 | 142.0 | 144.0 | 141.0 | 151.0 |
| 8 | 25.0 | 20.0 | 35.0 | 32.0 | 122.0 | 156.0 | 132.0 | 170.0 |
| 9 | 20.0 | 22.0 | 32.0 | 30.0 | 150.0 | 160.0 | 165.0 | 150.0 |
| 10 | 17.0 | 20.0 | 35.0 | 30.0 | 130.0 | 162.0 | 126.0 | 144.0 |
| 11 | 20.0 | 15.0 | 34.0 | 34.0 | 150.0 | 151.0 | 152.0 | 139.0 |
| 12 | 19.0 | 19.0 | 35.0 | 32.0 | 149.0 | 172.0 | 130.0 | 130.0 |
| 13 | 19.0 | 30.0 | 34.0 | 32.0 | 140.0 | 162.0 | 120.0 | 155.0 |
| 14 | 18.0 | 21.0 | 30.0 | 31.0 | 136.0 | 139.0 | 128.0 | 139.0 |
| 15 | 15.0 | 30.0 | 32.0 | 35.0 | 130.0 | 149.0 | 115.0 | 145.0 |
| 16 | 25.0 | 25.0 | 33.0 | 32.0 | 150.0 | 146.0 | 136.0 | 134.0 |
| 17 | 15.0 | 20.0 | 34.0 | 34.0 | 160.0 | 172.0 | 120.0 | 130.0 |
| 18 | 20.0 | 21.0 | 35.0 | 31.0 | 146.0 | 172.0 | 122.0 | 141.0 |
| 19 | 22.0 | 25.0 | 32.0 | 32.0 | 162.0 | 165.0 | 140.0 | 149.0 |
| 20 | 18.0 | 18.0 | 35.0 | 32.0 | 151.0 | 156.0 | 121.0 | 139.0 |
| 21 | 20.0 | 20.0 | 35.0 | 31.0 | 160.0 | 156.0 | 122.0 | 139.0 |

TABLE 6-continued

| | | | | | | | | |
|---|---|---|---|---|---|---|---|---|
| 22 | 16.0 | 21.0 | 39.0 | 34.0 | 150.0 | 165.0 | 120.0 | 169.0 |
| 23 | 20.0 | 31.0 | 36.0 | 35.0 | 160.0 | 180.0 | 149.0 | 156.0 |
| 24 | 20.0 | 20.0 | 30.0 | 32.0 | 160.0 | 160.0 | 136.0 | 135.0 |
| Average | 18.8 | 22.3 | 33.5 | 32.2 | 143.8 | 157.9 | 133.4 | 148.4 |
| Stan dev | 3.17 | 4.42 | 2.09 | 1.79 | 13.17 | 13.05 | 13.47 | 13.92 |
| T test | 3.16E−03 | | 2.60E−02 | | 5.04E−04 | | 4.19E−04 | |

| | Date Mature | Days to Maturity | Color |
|---|---|---|---|
| PAG02-23 | 12/9 | 80 | 5gy5/8 |
| SunDevil | 12/12 | 83 | 5gy1/6 |

| | Avg Head Diameter (mm) | | Avg Head Diam Core Length | | Frame Diam (cm) | | Head wt (g) | |
|---|---|---|---|---|---|---|---|---|
| | PAG02-23 | SunDevil | PAG02-23 | SunDevil | PAG02-23 | SunDevil | PAG02-23 | SunDevil |
| 1 | 148.0 | 137.0 | 8.7 | 5.5 | 45 | 44 | 545 | 665 |
| 2 | 140.5 | 170.0 | 9.4 | 11.3 | 41 | 44 | 402 | 709 |
| 3 | 142.5 | 140.0 | 9.5 | 7.0 | 43 | 45 | 538 | 652 |
| 4 | 123.5 | 160.5 | 6.2 | 7.3 | 45 | 46 | 399 | 635 |
| 5 | 126.5 | 168.5 | 8.4 | 7.7 | 42 | 48 | 575 | 610 |
| 6 | 132.0 | 161.0 | 8.3 | 6.0 | 48 | 49 | 653 | 685 |
| 7 | 141.5 | 147.5 | 5.7 | 7.4 | 44 | 45 | 460 | 627 |
| 8 | 127.0 | 163.0 | 5.1 | 5.8 | 45 | 46 | 732 | 611 |
| 9 | 157.5 | 155.0 | 7.9 | 7.8 | 44 | 48 | 782 | 646 |
| 10 | 128.0 | 153.0 | 7.5 | 7.0 | 47 | 45 | 783 | 597 |
| 11 | 151.0 | 145.0 | 7.6 | 7.3 | 44 | 44 | 743 | 903 |
| 12 | 139.5 | 151.0 | 7.3 | 10.1 | 47 | 46 | 690 | 674 |
| 13 | 130.0 | 158.5 | 6.8 | 8.3 | 42 | 49 | 515 | 760 |
| 14 | 132.0 | 139.0 | 7.3 | 4.6 | 46 | 42 | 700 | 610 |
| 15 | 122.5 | 147.0 | 8.2 | 7.0 | 44 | 43 | 663 | 739 |
| 16 | 143.0 | 140.0 | 5.7 | 4.7 | 45 | 45 | 544 | 676 |
| 17 | 140.0 | 151.0 | 9.3 | 7.6 | 46 | 46 | 647 | 667 |
| 18 | 134.0 | 156.5 | 6.7 | 7.5 | 42 | 49 | 665 | 628 |
| 19 | 151.0 | 157.0 | 6.9 | 6.3 | 40 | 49 | 754 | 674 |
| 20 | 136.0 | 147.5 | 7.6 | 8.2 | 47 | 49 | 641 | 694 |
| 21 | 141.0 | 147.5 | 7.1 | 7.4 | 46 | 50 | 671 | 663 |
| 22 | 135.0 | 167.0 | 8.4 | 8.0 | 45 | 51 | 732 | 596 |
| 23 | 154.5 | 168.0 | 7.7 | 5.4 | 44 | 50 | 501 | 652 |
| 24 | 150.0 | 145.3 | 7.7 | 7.3 | 49 | 49 | 673 | 638 |
| Average | 138.6 | 153.2 | 7.5 | 7.2 | 44.4 | 46.8 | 625.3 | 667.1 |
| Stan dev | 9.89 | 9.95 | 1.16 | 1.51 | 2.02 | 2.52 | 114.29 | 65.27 |
| T test | 6.31E−04 | | 3.64E−01 | | 9.39E−04 | | 1.27E−01 | |

TABLE 7

| Trial map #: | YM00025 | Location: | Yuma Valley | Ranch/lot: | Huber 5 | Date evald: | 12/6 |
|---|---|---|---|---|---|---|---|
| Wet Date: | 9/20 | Grower: | Mission Ranches | Commercial Var: | Raider | Eval by: | dg/jt |

| | Core length (mm) | | Core diam (mm) | | Head diam (mm) | | Head length (mm) | |
|---|---|---|---|---|---|---|---|---|
| Sample # | VanPire | SunDevil | VanPire | SunDevil | VanPire | SunDevil | VanPire | SunDevil |
| 1 | 20.0 | 25.0 | 34.0 | 30.0 | 135.0 | 134.0 | 114.0 | 140.0 |
| 2 | 25.0 | 15.0 | 34.0 | 33.0 | 160.0 | 175.0 | 129.0 | 163.0 |
| 3 | 25.0 | 20.0 | 41.0 | 31.0 | 140.0 | 129.0 | 131.0 | 151.0 |
| 4 | 21.0 | 22.0 | 35.0 | 30.0 | 130.0 | 165.0 | 125.0 | 156.0 |
| 5 | 35.0 | 27.0 | 30.0 | 34.0 | 160.0 | 162.0 | 145.0 | 175.0 |
| 6 | 22.0 | 20.0 | 30.0 | 30.0 | 150.0 | 152.0 | 120.0 | 170.0 |
| 7 | 20.0 | 28.0 | 32.0 | 36.0 | 136.0 | 144.0 | 123.0 | 151.0 |
| 8 | 22.0 | 20.0 | 32.0 | 32.0 | 165.0 | 156.0 | 134.0 | 170.0 |
| 9 | 20.0 | 22.0 | 30.0 | 30.0 | 136.0 | 160.0 | 146.0 | 150.0 |
| 10 | 22.0 | 20.0 | 35.0 | 30.0 | 141.0 | 162.0 | 125.0 | 144.0 |
| 11 | 25.0 | 15.0 | 33.0 | 34.0 | 150.0 | 151.0 | 132.0 | 139.0 |
| 12 | 18.0 | 19.0 | 34.0 | 32.0 | 125.0 | 172.0 | 135.0 | 130.0 |
| 13 | 22.0 | 30.0 | 36.0 | 32.0 | 160.0 | 162.0 | 139.0 | 155.0 |
| 14 | 31.0 | 21.0 | 30.0 | 31.0 | 181.0 | 139.0 | 120.0 | 139.0 |
| 15 | 20.0 | 30.0 | 31.0 | 35.0 | 170.0 | 149.0 | 141.0 | 145.0 |
| 16 | 22.0 | 25.0 | 31.0 | 32.0 | 135.0 | 146.0 | 134.0 | 134.0 |
| 17 | 20.0 | 20.0 | 30.0 | 34.0 | 180.0 | 172.0 | 122.0 | 130.0 |
| 18 | 25.0 | 21.0 | 34.0 | 31.0 | 150.0 | 172.0 | 118.0 | 141.0 |
| 19 | 30.0 | 25.0 | 32.0 | 32.0 | 160.0 | 165.0 | 131.0 | 149.0 |
| 20 | 21.0 | 18.0 | 35.0 | 32.0 | 139.0 | 156.0 | 125.0 | 139.0 |
| 21 | 31.0 | 20.0 | 36.0 | 31.0 | 132.0 | 156.0 | 130.0 | 139.0 |

TABLE 7-continued

| | | | | | | | | |
|---|---|---|---|---|---|---|---|---|
| 22 | 20.0 | 21.0 | 35.0 | 34.0 | 139.0 | 165.0 | 121.0 | 169.0 |
| 23 | 25.0 | 31.0 | 28.0 | 35.0 | 146.0 | 180.0 | 126.0 | 156.0 |
| 24 | 26.0 | 20.0 | 35.0 | 32.0 | 154.0 | 186.0 | 141.0 | 125.0 |
| Average | 23.7 | 22.3 | 33.0 | 32.2 | 148.9 | 157.9 | 129.5 | 148.4 |
| Stan Dev | $4.33 | $4.42 | $2.85 | $1.79 | $15.47 | $13.05 | $8.71 | $13.92 |
| T test | 2.82E−01 | | 2.32E−01 | | 3.46E−02 | | 9.49E−07 | |

| | Date Mature | Days to Maturity | Color |
|---|---|---|---|
| VanPire | 12/14 | 85 | 5gy4/4 |
| SunDevil | 12/12 | 83 | 5gy4/6 |

| | Avg Head Diameter (mm) | | Avg Head Diam Core Length | | Frame Diam (cm) | | Head wt (g) | |
|---|---|---|---|---|---|---|---|---|
| | VanPire | SunDevil | VanPire | SunDevil | VanPire | SunDevil | VanPire | SunDevil |
| 1 | 124.5 | 137.0 | 6.2 | 5.5 | 47 | 44 | 667 | 665 |
| 2 | 144.5 | 170.0 | 5.8 | 11.3 | 48 | 44 | 585 | 709 |
| 3 | 135.5 | 140.0 | 5.4 | 7.0 | 44 | 45 | 416 | 652 |
| 4 | 127.5 | 160.5 | 6.1 | 7.3 | 48 | 46 | 476 | 635 |
| 5 | 152.5 | 168.5 | 4.4 | 7.7 | 44 | 48 | 684 | 610 |
| 6 | 135.0 | 161.0 | 6.1 | 6.0 | 50 | 49 | 499 | 685 |
| 7 | 129.5 | 147.5 | 6.5 | 7.4 | 43 | 45 | 449 | 627 |
| 8 | 149.5 | 163.0 | 6.8 | 5.8 | 43 | 46 | 510 | 611 |
| 9 | 141.0 | 155.0 | 7.1 | 7.8 | 48 | 48 | 402 | 646 |
| 10 | 133.0 | 153.0 | 6.0 | 7.0 | 46 | 45 | 568 | 597 |
| 11 | 141.0 | 145.0 | 5.6 | 7.3 | 45 | 44 | 389 | 903 |
| 12 | 130.0 | 151.0 | 7.2 | 10.1 | 48 | 46 | 562 | 674 |
| 13 | 149.5 | 158.5 | 6.8 | 8.3 | 44 | 49 | 654 | 760 |
| 14 | 150.5 | 139.0 | 4.9 | 4.6 | 52 | 42 | 430 | 610 |
| 15 | 155.5 | 147.0 | 7.8 | 7.0 | 46 | 43 | 448 | 739 |
| 16 | 134.5 | 140.0 | 6.1 | 4.7 | 49 | 45 | 408 | 676 |
| 17 | 151.0 | 151.0 | 7.6 | 7.6 | 48 | 46 | 475 | 667 |
| 18 | 134.0 | 156.5 | 5.4 | 7.5 | 48 | 49 | 562 | 628 |
| 19 | 145.5 | 157.0 | 4.9 | 6.3 | 45 | 49 | 506 | 674 |
| 20 | 132.0 | 147.5 | 6.3 | 8.2 | 50 | 49 | 604 | 694 |
| 21 | 131.0 | 147.5 | 4.2 | 7.4 | 47 | 50 | 584 | 663 |
| 22 | 130.0 | 167.0 | 6.5 | 8.0 | 50 | 51 | 633 | 596 |
| 23 | 136.0 | 168.0 | 5.4 | 5.4 | 46 | 50 | 900 | 652 |
| 24 | 147.5 | 145.5 | 5.7 | 7.3 | 46 | 49 | 463 | 638 |
| Average | 139.2 | 153.2 | 6.0 | 7.2 | 46.9 | 46.8 | 536.4 | 667.1 |
| Stan Dev | $9.16 | $9.95 | $0.93 | $1.51 | $2.40 | $2.52 | $117.79 | $65.27 |
| T test | 7.09E−06 | | 2.80E−03 | | 8.61E−01 | | 1.99E−05 | |

TABLE 8

| Trial map #: | YM00025 | Location: | Yuma Valley | Ranch/lot: | Huber 5 | Date evald: | 12/6 |
|---|---|---|---|---|---|---|---|
| Wet Date: | 9/20 | Grower: | Mission Ranches | Commercial Var: | Raider | Eval by: | dg/jt |

| | Core length (mm) | | Core diam (mm) | | Head diam (mm) | | Head length (mm) | |
|---|---|---|---|---|---|---|---|---|
| Sample # | Raider | SunDevil | Raider | SunDevil | Raider | SunDevil | Raider | SunDevil |
| 1 | 31.0 | 25.0 | 39.0 | 30.0 | 140.0 | 134.0 | 154.0 | 140.0 |
| 2 | 25.0 | 15.0 | 35.0 | 33.0 | 130.0 | 175.0 | 134.0 | 165.0 |
| 3 | 15.0 | 20.0 | 32.0 | 31.0 | 122.0 | 129.0 | 121.0 | 151.0 |
| 4 | 15.0 | 22.0 | 34.0 | 30.0 | 140.0 | 165.0 | 140.0 | 156.0 |
| 5 | 25.0 | 27.0 | 33.0 | 34.0 | 150.0 | 162.0 | 140.0 | 175.0 |
| 6 | 30.0 | 20.0 | 32.0 | 30.0 | 131.0 | 152.0 | 134.0 | 170.0 |
| 7 | 28.0 | 28.0 | 35.0 | 36.0 | 145.0 | 144.0 | 121.0 | 151.0 |
| 8 | 22.0 | 20.0 | 40.0 | 32.0 | 117.0 | 156.0 | 135.0 | 170.0 |
| 9 | 28.0 | 22.0 | 28.0 | 30.0 | 130.0 | 160.0 | 131.0 | 150.0 |
| 10 | 25.0 | 20.0 | 32.0 | 30.0 | 142.0 | 162.0 | 136.0 | 144.0 |
| 11 | 34.0 | 15.0 | 27.0 | 34.0 | 135.0 | 151.0 | 160.0 | 139.0 |
| 12 | 30.0 | 19.0 | 39.0 | 32.0 | 149.0 | 172.0 | 128.0 | 130.0 |
| 13 | 22.0 | 30.0 | 36.0 | 32.0 | 144.0 | 162.0 | 140.0 | 155.0 |
| 14 | 34.0 | 21.0 | 30.0 | 31.0 | 169.0 | 139.0 | 135.0 | 139.0 |
| 15 | 20.0 | 30.0 | 37.0 | 35.0 | 140.0 | 149.0 | 125.0 | 145.0 |
| 16 | 36.0 | 25.0 | 38.0 | 32.0 | 155.0 | 146.0 | 149.0 | 134.0 |
| 17 | 15.0 | 20.0 | 36.0 | 34.0 | 133.0 | 172.0 | 120.0 | 130.0 |
| 18 | 40.0 | 21.0 | 37.0 | 31.0 | 155.0 | 172.0 | 142.0 | 141.0 |
| 19 | 26.0 | 25.0 | 34.0 | 32.0 | 125.0 | 165.0 | 120.0 | 149.0 |
| 20 | 25.0 | 18.0 | 30.0 | 32.0 | 150.0 | 156.0 | 130.0 | 139.0 |
| 21 | 23.0 | 20.0 | 34.0 | 31.0 | 142.0 | 156.0 | 126.0 | 139.0 |

TABLE 8-continued

| | | | | | | | | |
|---|---|---|---|---|---|---|---|---|
| 22 | 23.0 | 21.0 | 37.0 | 34.0 | 140.0 | 165.0 | 132.0 | 169.0 |
| 23 | 27.0 | 31.0 | 35.0 | 35.0 | 159.0 | 180.0 | 140.0 | 156.0 |
| 24 | 20.0 | 20.0 | 31.0 | 32.0 | 136.0 | 160.0 | 125.0 | 125.0 |
| Average | 26.2 | 22.3 | 34.2 | 32.2 | 140.8 | 157.9 | 134.2 | 148.4 |
| Stan dev | 6.45 | 4.42 | 3.48 | 1.79 | 12.19 | 13.05 | 10.40 | 13.92 |
| T test | 1.80E–02 | | 1.59E–02 | | 2.41E–5 | | 2.24E–04 | |

| | Date Mature | Days to Maturity | Color |
|---|---|---|---|
| Raider | 12/9/2000 | 80 | 5gy5/6 |
| SunDevil | 12/12/2000 | 83 | 5gy4/6 |

| | Avg Head Diameter (mm) | | Avg Head Diam Core Length | | Frame Diam (cm) | | Head wt (g) | |
|---|---|---|---|---|---|---|---|---|
| | Raider | SunDevil | Raider | SunDevil | Raider | SunDevil | Raider | SunDevil |
| 1 | 147.0 | 137.0 | 4.7 | 5.5 | 37 | 44 | 490 | 665 |
| 2 | 132.0 | 170.0 | 5.3 | 11.3 | 47 | 44 | 700 | 709 |
| 3 | 121.5 | 140.0 | 8.1 | 7.0 | 46 | 45 | 701 | 652 |
| 4 | 140.0 | 160.5 | 9.3 | 7.3 | 45 | 46 | 730 | 635 |
| 5 | 145.0 | 168.5 | 5.8 | 7.7 | 46 | 48 | 553 | 610 |
| 6 | 132.5 | 161.0 | 4.4 | 6.0 | 45 | 49 | 621 | 685 |
| 7 | 133.0 | 147.5 | 4.8 | 7.4 | 44 | 45 | 790 | 627 |
| 8 | 126.0 | 163.0 | 5.7 | 5.8 | 45 | 46 | 892 | 611 |
| 9 | 130.5 | 155.0 | 4.7 | 7.8 | 46 | 48 | 620 | 646 |
| 10 | 139.0 | 153.0 | 5.6 | 7.0 | 45 | 45 | 651 | 597 |
| 11 | 147.5 | 145.0 | 4.3 | 7.3 | 44 | 44 | 659 | 903 |
| 12 | 138.5 | 151.0 | 4.6 | 10.1 | 42 | 46 | 703 | 674 |
| 13 | 142.0 | 158.5 | 6.5 | 8.3 | 40 | 49 | 600 | 760 |
| 14 | 152.0 | 139.0 | 4.5 | 4.6 | 45 | 42 | 432 | 610 |
| 15 | 132.5 | 147.0 | 6.6 | 7.0 | 43 | 43 | 740 | 739 |
| 16 | 152.0 | 140.0 | 4.2 | 4.7 | 42 | 45 | 551 | 676 |
| 17 | 126.5 | 151.0 | 8.4 | 7.6 | 46 | 46 | 700 | 667 |
| 18 | 148.5 | 156.5 | 3.7 | 7.5 | 45 | 49 | 985 | 628 |
| 19 | 122.5 | 157.0 | 4.7 | 6.3 | 41 | 49 | 572 | 674 |
| 20 | 140.0 | 147.5 | 5.6 | 8.2 | 45 | 49 | 517 | 694 |
| 21 | 134.0 | 147.5 | 5.8 | 7.4 | 43 | 50 | 604 | 663 |
| 22 | 136.0 | 167.0 | 5.9 | 8.0 | 46 | 51 | 660 | 596 |
| 23 | 149.5 | 168.0 | 5.5 | 5.4 | 44 | 50 | 950 | 652 |
| 24 | 132.0 | 145.5 | 4.4 | 7.3 | 44 | 49 | 623 | 638 |
| Average | 137.5 | 153.2 | 5.6 | 7.2 | 44.0 | 46.8 | 668.5 | 667.1 |
| Stan dev | 9.08 | 9.95 | 1.41 | 1.51 | 2.28 | 2.52 | 135.21 | 65.27 |
| T test | 8.21E–07 | | 3.71E–04 | | 2.60E–04 | | 9.64E–01 | |

TABLE 9

| Trial map #: | YPD00022 | Location: | Gila | Ranch/lot: | Ferguson/20 | Date evald: | 12/21 |
|---|---|---|---|---|---|---|---|
| Wet Date: | 9/27 | Grower: | SMT | Commercial Var: | Domingos 7/11 | Eval by: | JT |

| | Core length (mm) | | Core diam (mm) | | Head diam (mm) | | Head length (mm) | |
|---|---|---|---|---|---|---|---|---|
| Sample # | Sun Devil | EarlySun Devil | Sun Devil | EarlySun Devil | Sun Devil | EarlySun Devil | Sun Devil | EarlySun Devil |
| 1 | 30.0 | 25.0 | 35.0 | 29.0 | 120.0 | 134.0 | 130.0 | 130.0 |
| 2 | 25.0 | 28.0 | 34.0 | 31.0 | 130.0 | 125.0 | 120.0 | 135.0 |
| 3 | 26.0 | 25.0 | 34.0 | 30.0 | 130.0 | 116.0 | 150.0 | 135.0 |
| 4 | 20.0 | 35.0 | 34.0 | 35.0 | 130.0 | 120.0 | 125.0 | 130.0 |
| 5 | 26.0 | 20.0 | 30.0 | 31.0 | 135.0 | 118.0 | 130.0 | 120.0 |
| 6 | 25.0 | 30.0 | 37.0 | 34.0 | 145.0 | 121.0 | 130.0 | 131.0 |
| 7 | 24.0 | 29.0 | 37.0 | 34.0 | 135.0 | 120.0 | 145.0 | 140.0 |
| 8 | 25.0 | 32.0 | 36.0 | 30.0 | 125.0 | 125.0 | 130.0 | 140.0 |
| 9 | 25.0 | 28.0 | 33.0 | 31.0 | 140.0 | 115.0 | 133.0 | 126.0 |
| 10 | 25.0 | 35.0 | 29.0 | 34.0 | 125.0 | 115.0 | 122.0 | 135.0 |
| 11 | 24.0 | 30.0 | 33.0 | 34.0 | 122.0 | 125.0 | 120.0 | 125.0 |
| 12 | 27.0 | 36.0 | 30.0 | 32.0 | 139.0 | 115.0 | 140.0 | 125.0 |
| 13 | 20.0 | 35.0 | 31.0 | 31.0 | 139.0 | 145.0 | 120.0 | 140.0 |
| 14 | 20.0 | 27.0 | 37.0 | 36.0 | 125.0 | 125.0 | 120.0 | 122.0 |
| 15 | 25.0 | 24.0 | 33.0 | 34.0 | 115.0 | 110.0 | 118.0 | 124.0 |
| 16 | 32.0 | 30.0 | 30.0 | 30.0 | 130.0 | 135.0 | 144.0 | 130.0 |
| 17 | 25.0 | 28.0 | 34.0 | 34.0 | 135.0 | 125.0 | 130.0 | 130.0 |
| 18 | 27.0 | 30.0 | 30.0 | 31.0 | 132.0 | 100.0 | 130.0 | 125.0 |
| 19 | 22.0 | 32.0 | 30.0 | 34.0 | 125.0 | 120.0 | 120.0 | 140.0 |
| 20 | 21.0 | 34.0 | 29.0 | 33.0 | 128.0 | 135.0 | 125.0 | 140.0 |

TABLE 9-continued

| | | | | | | | | |
|---|---|---|---|---|---|---|---|---|
| 21 | 20.0 | 25.0 | 34.0 | 30.0 | 124.0 | 120.0 | 125.0 | 125.0 |
| 22 | 28.0 | 20.0 | 32.0 | 30.0 | 130.0 | 115.0 | 125.0 | 120.0 |
| 23 | 26.0 | 33.0 | 31.0 | 29.0 | 120.0 | 119.0 | 130.0 | 140.0 |
| 24 | 25.0 | 36.0 | 20.0 | 30.0 | 120.0 | 120.0 | 140.0 | 140.0 |
| Average | 24.7 | 29.5 | 32.6 | 32.0 | 129.1 | 121.6 | 129.3 | 131.2 |
| Stan dev | 3.09 | 4.69 | 2.62 | 2.10 | 7.45 | 9.23 | 8.91 | 7.10 |
| T test | 1.44E−04 | | 3.35E−01 | | 3.16E−03 | | 4.14E−01 | |

| | Date Mature | Days to Maturity | Color |
|---|---|---|---|
| Sun Devil | 12/21 | 85 | 5gy4/8 |
| EarlySun Devil | 12/21 | 85 | 5gy4/8 |

| | Avg Head Diameter (mm) | | Avg Head Diam Core Length | | Frame Diam (cm) | | Head wt (g) | |
|---|---|---|---|---|---|---|---|---|
| Sample # | Sun Devil | EarlySun Devil | Sun Devil | EarlySun Devil | Sun Devil | EarlySun Devil | Sun Devil | EarlySun Devil |
| 1 | 125.0 | 132.0 | 4.2 | 5.3 | 38 | 39 | 600 | 752 |
| 2 | 125.0 | 130.0 | 5.0 | 4.6 | 36 | 37 | 600 | 581 |
| 3 | 140.0 | 125.5 | 5.4 | 5.0 | 37 | 36 | 620 | 695 |
| 4 | 127.5 | 125.0 | 6.4 | 3.6 | 40 | 37 | 400 | 578 |
| 5 | 132.5 | 119.0 | 5.1 | 3.4 | 42 | 37 | 470 | 780 |
| 6 | 137.5 | 126.0 | 5.5 | 6.3 | 45 | 33 | 460 | 452 |
| 7 | 140.0 | 130.0 | 5.8 | 4.3 | 30 | 37 | 600 | 577 |
| 8 | 127.5 | 132.5 | 5.1 | 4.6 | 35 | 39 | 710 | 665 |
| 9 | 136.5 | 120.5 | 5.5 | 3.8 | 39 | 38 | 820 | 640 |
| 10 | 123.5 | 125.0 | 4.9 | 4.5 | 38 | 29 | 537 | 524 |
| 11 | 121.0 | 125.0 | 5.0 | 3.6 | 41 | 43 | 645 | 489 |
| 12 | 139.5 | 120.0 | 5.2 | 4.0 | 38 | 37 | 640 | 555 |
| 13 | 129.5 | 142.5 | 6.5 | 4.0 | 41 | 37 | 675 | 719 |
| 14 | 122.5 | 123.5 | 6.1 | 3.5 | 46 | 34 | 370 | 645 |
| 15 | 116.5 | 117.0 | 4.7 | 4.3 | 38 | 40 | 690 | 473 |
| 16 | 137.0 | 132.5 | 4.3 | 5.5 | 38 | 42 | 340 | 543 |
| 17 | 132.5 | 127.5 | 5.3 | 4.6 | 41 | 34 | 820 | 566 |
| 18 | 131.0 | 112.5 | 4.9 | 3.8 | 39 | 34 | 660 | 721 |
| 19 | 122.5 | 130.0 | 5.6 | 4.1 | 38 | 38 | 750 | 638 |
| 20 | 126.5 | 137.5 | 6.0 | 4.0 | 34 | 37 | 555 | 662 |
| 21 | 124.5 | 122.5 | 6.2 | 4.9 | 38 | 35 | 660 | 380 |
| 22 | 127.5 | 117.5 | 4.6 | 5.9 | 38 | 33 | 580 | 710 |
| 23 | 125.0 | 129.5 | 4.8 | 3.9 | 32 | 35 | 734 | 372 |
| 24 | 130.0 | 130.0 | 5.2 | 3.6 | 40 | 35 | 695 | 638 |
| Average | 129.2 | 126.4 | 5.3 | 4.4 | 38.4 | 36.5 | 609.6 | 598.2 |
| Stan dev | 6.56 | 6.83 | 0.63 | 0.78 | 3.56 | 3.05 | 129.30 | 111.18 |
| T test | 1.52E−01 | | 4.44E−05 | | 4.65E−02 | | 7.44E−01 | |

TABLE 10

| Trial map #: | YPD00022 | Location: | Gila | Ranch/lot: | Ferguson/20 | Date evald: | 12/21 |
|---|---|---|---|---|---|---|---|
| Wet Date: | 9/27 | Grower: | SMT | Commercial Var: | Domingos 7/11 | Eval by: | JT |

| | Core length (mm) | | Core diam (mm) | | Head diam (mm) | | Head length (mm) | |
|---|---|---|---|---|---|---|---|---|
| Sample # | Sun Devil | PAG02-23 | Sun Devil | PAG02-23 | Sun Devil | PAG02-23 | Sun Devil | PAG02-23 |
| 1 | 30.0 | 25.0 | 35.0 | 31.0 | 120.0 | 120.0 | 130.0 | 120.0 |
| 2 | 25.0 | 23.0 | 24.0 | 30.0 | 130.0 | 128.0 | 120.0 | 125.0 |
| 3 | 26.0 | 26.0 | 34.0 | 31.0 | 130.0 | 120.0 | 150.0 | 115.0 |
| 4 | 20.0 | 30.0 | 34.0 | 33.0 | 130.0 | 120.0 | 125.0 | 115.0 |
| 5 | 26.0 | 20.0 | 30.0 | 30.0 | 135.0 | 108.0 | 130.0 | 100.0 |
| 6 | 25.0 | 22.0 | 37.0 | 30.0 | 145.0 | 110.0 | 130.0 | 105.0 |
| 7 | 24.0 | 30.0 | 37.0 | 30.0 | 135.0 | 135.0 | 145.0 | 130.0 |
| 8 | 25.0 | 20.0 | 36.0 | 37.0 | 125.0 | 120.0 | 130.0 | 115.0 |
| 9 | 25.0 | 22.0 | 33.0 | 33.0 | 140.0 | 132.0 | 133.0 | 110.0 |
| 10 | 25.0 | 30.0 | 29.0 | 30.0 | 125.0 | 110.0 | 122.0 | 109.0 |
| 11 | 24.0 | 30.0 | 33.0 | 37.0 | 122.0 | 130.0 | 120.0 | 140.0 |
| 12 | 27.0 | 25.0 | 30.0 | 29.0 | 139.0 | 110.0 | 140.0 | 115.0 |
| 13 | 20.0 | 25.0 | 31.0 | 30.0 | 139.0 | 120.0 | 120.0 | 125.0 |
| 14 | 20.0 | 20.0 | 37.0 | 38.0 | 125.0 | 130.0 | 120.0 | 130.0 |
| 15 | 25.0 | 20.0 | 33.0 | 36.0 | 115.0 | 105.0 | 118.0 | 115.0 |
| 16 | 32.0 | 25.0 | 30.0 | 33.0 | 130.0 | 120.0 | 144.0 | 115.0 |
| 17 | 25.0 | 20.0 | 34.0 | 32.0 | 135.0 | 110.0 | 130.0 | 105.0 |
| 18 | 27.0 | 28.0 | 30.0 | 31.0 | 132.0 | 130.0 | 130.0 | 125.0 |

TABLE 10-continued

| | | | | | | | | |
|---|---|---|---|---|---|---|---|---|
| 19 | 22.0 | 25.0 | 30.0 | 31.0 | 125.0 | 120.0 | 120.0 | 125.0 |
| 20 | 21.0 | 19.0 | 29.0 | 30.0 | 128.0 | 115.0 | 125.0 | 100.0 |
| 21 | 20.0 | 30.0 | 34.0 | 34.0 | 124.0 | 130.0 | 125.0 | 120.0 |
| 22 | 28.0 | 18.0 | 32.0 | 31.0 | 130.0 | 118.0 | 125.0 | 100.0 |
| 23 | 26.0 | 36.0 | 31.0 | 32.0 | 120.0 | 130.0 | 130.0 | 140.0 |
| 24 | 26.0 | 34.0 | 30.0 | 30.0 | 120.0 | 130.0 | 140.0 | 140.0 |
| Average | 24.7 | 25.1 | 32.6 | 32.0 | 129.1 | 121.0 | 129.3 | 118.5 |
| Stan dev | 3.09 | 4.97 | 2.62 | 2.60 | 7.45 | 9.09 | 8.91 | 12.76 |
| T test | 7.29E−01 | | 4.42E−01 | | 1.53E−03 | | 1.53E−03 | |

| | Date Mature | Days to Maturity | Color |
|---|---|---|---|
| Sun Devil | 12/21 | 85 | 5gy4/8 |
| PAG02-23 | 12/19 | 83 | 5gy5/6 |

| | Avg Head Diameter (mm) | | Avg Head Diam Core Length | | Frame Diam (cm) | | Head wt (g) | |
|---|---|---|---|---|---|---|---|---|
| Sample # | Sun Devil | PAG02-23 | Sun Devil | PAG02-23 | Sun Devil | PAG02-23 | Sun Devil | PAG02-23 |
| 1 | 125.0 | 120.0 | 4.2 | 4.8 | 38 | 34 | 600 | 712 |
| 2 | 125.0 | 126.5 | 5.0 | 5.5 | 36 | 35 | 600 | 640 |
| 3 | 140.0 | 117.5 | 5.4 | 4.5 | 37 | 40 | 620 | 600 |
| 4 | 127.5 | 117.5 | 6.4 | 3.9 | 40 | 41 | 400 | 528 |
| 5 | 132.5 | 104.0 | 5.1 | 3.5 | 42 | 39 | 470 | 833 |
| 6 | 137.5 | 107.5 | 5.5 | 5.4 | 45 | 33 | 460 | 499 |
| 7 | 140.0 | 132.5 | 5.8 | 6.0 | 30 | 42 | 600 | 669 |
| 8 | 127.5 | 117.5 | 5.1 | 3.9 | 35 | 38 | 710 | 545 |
| 9 | 136.5 | 121.0 | 5.5 | 6.1 | 39 | 33 | 820 | 620 |
| 10 | 123.5 | 109.5 | 4.9 | 5.0 | 38 | 31 | 537 | 775 |
| 11 | 121.0 | 135.0 | 5.0 | 4.5 | 41 | 40 | 645 | 522 |
| 12 | 139.5 | 112.5 | 5.2 | 3.8 | 38 | 40 | 640 | 545 |
| 13 | 129.5 | 122.5 | 6.5 | 4.9 | 41 | 39 | 675 | 725 |
| 14 | 122.5 | 130.0 | 6.1 | 5.2 | 46 | 42 | 370 | 526 |
| 15 | 116.5 | 110.0 | 4.7 | 5.5 | 38 | 41 | 690 | 410 |
| 16 | 137.0 | 117.5 | 4.3 | 5.9 | 38 | 37 | 340 | 506 |
| 17 | 132.5 | 107.5 | 5.3 | 5.4 | 41 | 39 | 820 | 725 |
| 18 | 131.0 | 127.5 | 4.9 | 4.6 | 39 | 39 | 660 | 694 |
| 19 | 122.5 | 122.5 | 5.6 | 4.9 | 38 | 40 | 750 | 460 |
| 20 | 126.5 | 107.5 | 6.0 | 5.7 | 34 | 40 | 555 | 610 |
| 21 | 124.5 | 125.0 | 6.2 | 4.2 | 38 | 37 | 660 | 564 |
| 22 | 127.5 | 109.0 | 4.6 | 6.1 | 38 | 39 | 580 | 715 |
| 23 | 125.0 | 135.0 | 4.8 | 3.8 | 32 | 43 | 734 | 560 |
| 24 | 130.0 | 140.0 | 5.2 | 4.3 | 40 | 39 | 695 | 600 |
| Average | 129.2 | 119.8 | 5.3 | 4.9 | 38.4 | 38.4 | 609.6 | 608.0 |
| Stan dev | 6.56 | 10.17 | 0.63 | 0.81 | 3.56 | 3.12 | 129.30 | 105.62 |
| T test | 4.20E−04 | | 4.57E−02 | | 9.66E−01 | | 9.62E−01 | |

TABLE 11

| Trial Map #: | YPD00022 | Location: | Gila | Ranch/lot: | | Ferguson/20 | Date evald: | | 12/21 |
|---|---|---|---|---|---|---|---|---|---|
| Wet Date: | | 9/27 | Grower: | SMT | Commercial Var: | Domingos 7/11 | Eval by: | | JT |

| | Core length (mm) | | Core diam (mm) | | Head diam (mm) | | Head length (mm) | | Avg. Head Diameter (mm) | |
|---|---|---|---|---|---|---|---|---|---|---|
| Sample # | Sun Devil | VanPire | Sun Devil | VanPire | Sun Devil | VanPire | Sun Devil | VanPire | Sun Devil | VanPire |
| 1 | 30.0 | 35.0 | 35.0 | 32.0 | 120.0 | 130.0 | 130.0 | 130.0 | 125.0 | 130.0 |
| 2 | 25.0 | 45.0 | 34.0 | 31.0 | 130.0 | 130.0 | 120.0 | 150.0 | 125.0 | 140.0 |
| 3 | 26.0 | 35.0 | 34.0 | 33.0 | 130.0 | 120.0 | 150.0 | 140.0 | 140.0 | 130.0 |
| 4 | 20.0 | 35.0 | 34.0 | 38.0 | 130.0 | 130.0 | 125.0 | 145.0 | 127.5 | 137.5 |
| 5 | 26.0 | 30.0 | 30.0 | 32.0 | 135.0 | 130.0 | 130.0 | 135.0 | 132.5 | 130.0 |
| 6 | 25.0 | 35.0 | 37.0 | 29.0 | 145.0 | 125.0 | 130.0 | 145.0 | 137.5 | 135.0 |
| 7 | 24.0 | 30.0 | 37.0 | 29.0 | 135.0 | 100.0 | 145.0 | 150.0 | 140.0 | 125.0 |
| 8 | 25.0 | 15.0 | 36.0 | 29.0 | 125.0 | 110.0 | 130.0 | 110.0 | 127.5 | 110.0 |
| 9 | 25.0 | 25.0 | 33.0 | 29.0 | 140.0 | 110.0 | 133.0 | 125.0 | 136.5 | 117.5 |
| 10 | 25.0 | 20.0 | 29.0 | 29.0 | 125.0 | 110.0 | 122.0 | 120.0 | 123.5 | 115.0 |
| 11 | 24.0 | 35.0 | 33.0 | 32.0 | 122.0 | 135.0 | 120.0 | 130.0 | 121.0 | 132.5 |
| 12 | 27.0 | 25.0 | 30.0 | 30.0 | 139.0 | 130.0 | 140.0 | 130.0 | 139.5 | 130.0 |
| 13 | 20.0 | 25.0 | 31.0 | 30.0 | 139.0 | 140.0 | 120.0 | 130.0 | 129.5 | 135.0 |
| 14 | 20.0 | 35.0 | 37.0 | 30.0 | 125.0 | 120.0 | 120.0 | 120.0 | 122.5 | 120.0 |
| 15 | 25.0 | 45.0 | 33.0 | 30.0 | 115.0 | 150.0 | 118.0 | 145.0 | 116.5 | 147.5 |
| 16 | 32.0 | 28.0 | 30.0 | 29.0 | 130.0 | 115.0 | 144.0 | 138.0 | 137.0 | 126.5 |
| 17 | 25.0 | 35.0 | 34.0 | 31.0 | 135.0 | 130.0 | 130.0 | 140.0 | 132.5 | 135.0 |
| 18 | 27.0 | 35.0 | 30.0 | 31.0 | 132.0 | 140.0 | 130.0 | 160.0 | 131.0 | 150.0 |
| 19 | 22.0 | 35.0 | 30.0 | 31.0 | 125.0 | 135.0 | 120.0 | 140.0 | 122.5 | 137.5 |

TABLE 11-continued

| | | | | | | | | | | |
|---|---|---|---|---|---|---|---|---|---|---|
| 20 | 21.0 | 30.0 | 29.0 | 29.0 | 128.0 | 120.0 | 125.0 | 130.0 | 126.5 | 125.0 |
| 21 | 20.0 | 28.0 | 34.0 | 30.0 | 124.0 | 115.0 | 125.0 | 120.0 | 124.5 | 117.5 |
| 22 | 28.0 | 25.0 | 32.0 | 32.0 | 130.0 | 110.0 | 125.0 | 125.0 | 127.5 | 117.5 |
| 23 | 26.0 | 30.0 | 31.0 | 30.0 | 120.0 | 105.0 | 130.0 | 150.0 | 125.0 | 127.5 |
| 24 | 25.0 | 30.0 | 30.0 | 32.0 | 120.0 | 110.0 | 140.0 | 125.0 | 130.0 | 117.5 |
| Average | 24.7 | 31.1 | 32.6 | 30.7 | 129.1 | 122.7 | 129.3 | 134.7 | 129.2 | 128.7 |
| Stan dev | 3.09 | 6.85 | 2.62 | 2.03 | 7.45 | 12.68 | 8.91 | 12.17 | 6.56 | 10.17 |
| T test | 1.39E-04 | | 6.82E-03 | | 3.79E-02 | | 8.28E-02 | | 8.47E-01 | |

| | Date Mature | Days to Maturity | Color |
|---|---|---|---|
| Sun Devil | 12/21 | 85 | 5gy4/8 |
| VanPire | 12/23 | 87 | 5gy4/4 |

| | | Avg. Head Diam Core Length | | Frame diam (cm) | | Head wt (g) | |
|---|---|---|---|---|---|---|---|
| | Sample # | Sun Devil | VanPire | Sun Devil | VanPire | Sun Devil | VanPire |
| | 1 | 4.2 | 3.7 | 38 | 41 | 600 | 950 |
| | 2 | 5.0 | 3.1 | 36 | 45 | 600 | 810 |
| | 3 | 5.4 | 3.7 | 37 | 40 | 620 | 840 |
| | 4 | 6.4 | 3.9 | 40 | 40 | 400 | 1010 |
| | 5 | 5.1 | 3.7 | 42 | 46 | 470 | 820 |
| | 6 | 5.5 | 4.5 | 45 | 45 | 460 | 540 |
| | 7 | 5.8 | 3.6 | 30 | 46 | 600 | 780 |
| | 8 | 5.1 | 3.7 | 35 | 43 | 710 | 650 |
| | 9 | 5.5 | 7.8 | 39 | 42 | 820 | 740 |
| | 10 | 4.9 | 4.6 | 38 | 39 | 537 | 750 |
| | 11 | 5.0 | 6.6 | 41 | 46 | 645 | 780 |
| | 12 | 5.2 | 3.7 | 38 | 45 | 640 | 780 |
| | 13 | 6.5 | 5.4 | 41 | 44 | 675 | 580 |
| | 14 | 6.1 | 4.8 | 46 | 39 | 370 | 540 |
| | 15 | 4.7 | 4.2 | 38 | 44 | 690 | 520 |
| | 16 | 4.3 | 2.8 | 38 | 44 | 340 | 665 |
| | 17 | 5.3 | 3.9 | 41 | 42 | 850 | 790 |
| | 18 | 4.9 | 4.3 | 39 | 45 | 660 | 440 |
| | 19 | 5.6 | 3.9 | 38 | 42 | 750 | 660 |
| | 20 | 6.0 | 4.2 | 34 | 40 | 555 | 645 |
| | 21 | 6.2 | 4.7 | 38 | 43 | 660 | 582 |
| | 22 | 4.6 | 4.7 | 38 | 43 | 580 | 700 |
| | 23 | 4.8 | 4.3 | 32 | 46 | 734 | 575 |
| | 24 | 5.2 | 3.9 | 40 | 42 | 695 | 425 |
| | Average | 5.3 | 4.3 | 38.4 | 43.0 | 609.6 | 690.5 |
| | Stan dev | 0.63 | 1.07 | 3.56 | 2.30 | 129.30 | 149.35 |
| | T test | 2.78E-04 | | 3.26E-06 | | 5.08E-02 | |

TABLE 12

| Trial Map #: | YPD00022 | Location: | Gila | Ranch/lot: | | Ferguson/20 | Date evald: | | 12/21 |
|---|---|---|---|---|---|---|---|---|---|
| Wet Date: | | 9/27 | Grower: | SMT | Commercial Var: | Domingos 7/11 | Eval by: | | JT |

| | Core length (mm) | | Core diam (mm) | | Head diam (mm) | | Head length (mm) | | Avg. Head Diameter (mm) | |
|---|---|---|---|---|---|---|---|---|---|---|
| Sample # | Sun Devil | Raider | Sun Devil | Raider | Sun Devil | Raider | Sun Devil | Raider | Sun Devil | Raider |
| 1 | 30.0 | 25.0 | 35.0 | 29.0 | 120.0 | 110.0 | 130.0 | 130.0 | 125.0 | 120.0 |
| 2 | 25.0 | 30.0 | 34.0 | 34.0 | 130.0 | 115.0 | 120.0 | 130.0 | 125.0 | 122.5 |
| 3 | 26.0 | 22.0 | 34.0 | 34.0 | 130.0 | 120.0 | 150.0 | 130.0 | 140.0 | 125.0 |
| 4 | 20.0 | 20.0 | 34.0 | 30.0 | 130.0 | 115.0 | 125.0 | 115.0 | 127.5 | 115.0 |
| 5 | 26.0 | 35.0 | 30.0 | 30.0 | 135.0 | 135.0 | 130.0 | 135.0 | 132.5 | 135.0 |
| 6 | 25.0 | 35.0 | 37.0 | 35.0 | 145.0 | 120.0 | 130.0 | 140.0 | 137.5 | 130.0 |
| 7 | 24.0 | 30.0 | 37.0 | 30.0 | 135.0 | 120.0 | 145.0 | 135.0 | 140.0 | 127.5 |
| 8 | 25.0 | 30.0 | 36.0 | 32.0 | 125.0 | 135.0 | 130.0 | 130.0 | 127.5 | 132.5 |
| 9 | 25.0 | 30.0 | 33.0 | 29.0 | 140.0 | 120.0 | 133.0 | 125.0 | 136.5 | 122.5 |
| 10 | 25.0 | 35.0 | 29.0 | 24.0 | 125.0 | 115.0 | 122.0 | 120.0 | 123.5 | 117.5 |
| 11 | 24.0 | 30.0 | 33.0 | 30.0 | 122.0 | 110.0 | 120.0 | 134.0 | 121.0 | 122.0 |
| 12 | 27.0 | 35.0 | 30.0 | 32.0 | 139.0 | 120.0 | 140.0 | 140.0 | 139.5 | 130.0 |
| 13 | 20.0 | 30.0 | 31.0 | 30.0 | 139.0 | 120.0 | 120.0 | 125.0 | 129.5 | 122.5 |
| 14 | 20.0 | 25.0 | 37.0 | 34.0 | 125.0 | 115.0 | 120.0 | 125.0 | 122.5 | 120.0 |
| 15 | 25.0 | 25.0 | 33.0 | 35.0 | 115.0 | 115.0 | 118.0 | 125.0 | 116.5 | 120.0 |
| 16 | 32.0 | 25.0 | 30.0 | 35.0 | 130.0 | 130.0 | 144.0 | 125.0 | 137.0 | 127.5 |
| 17 | 25.0 | 35.0 | 34.0 | 31.0 | 135.0 | 120.0 | 130.0 | 135.0 | 132.5 | 127.5 |
| 18 | 27.0 | 30.0 | 30.0 | 36.0 | 132.0 | 115.0 | 130.0 | 145.0 | 131.0 | 130.0 |
| 19 | 22.0 | 25.0 | 30.0 | 36.0 | 125.0 | 115.0 | 120.0 | 140.0 | 122.5 | 127.5 |

TABLE 12-continued

| | | | | | | | | | | |
|---|---|---|---|---|---|---|---|---|---|---|
| 20 | 21.0 | 35.0 | 29.0 | 30.0 | 128.0 | 120.0 | 125.0 | 140.0 | 126.5 | 130.0 |
| 21 | 20.0 | 25.0 | 34.0 | 35.0 | 124.0 | 130.0 | 125.0 | 150.0 | 124.5 | 140.0 |
| 22 | 28.0 | 30.0 | 32.0 | 35.0 | 130.0 | 110.0 | 125.0 | 130.0 | 127.5 | 120.0 |
| 23 | 26.0 | 25.0 | 31.0 | 30.0 | 120.0 | 110.0 | 130.0 | 130.0 | 125.0 | 120.0 |
| 24 | 25.0 | 30.0 | 30.0 | 32.0 | 120.0 | 130.0 | 140.0 | 110.0 | 130.0 | 120.0 |
| Average | 24.7 | 29.0 | 32.6 | 32.0 | 129.1 | 119.4 | 129.3 | 131.0 | 129.2 | 125.2 |
| Stan dev | 3.09 | 4.51 | 2.62 | 2.95 | 7.45 | 7.56 | 8.91 | 9.19 | 6.56 | 6.04 |
| T test | 3.24E-04 | | 4.41E-01 | | 4.62E-05 | | 5.06E-01 | | 3.31E-02 | |

| | Date Mature | Days to Maturity | Color |
|---|---|---|---|
| Sun Devil | 12/21 | 85 | 5gy4/8 |
| Raider | 12/19 | 83 | 5gy5/6 |

| | Avg. Head Diam Core Length | | Frame diam (cm) | | Head wt (g) | |
|---|---|---|---|---|---|---|
| Sample # | Sun Devil | Raider | Sun Devil | Raider | Sun Devil | Raider |
| 1 | 4.2 | 4.8 | 38 | 42 | 600 | 620 |
| 2 | 5.0 | 4.1 | 36 | 42 | 600 | 940 |
| 3 | 5.4 | 5.7 | 37 | 39 | 620 | 770 |
| 4 | 6.4 | 5.8 | 40 | 33 | 400 | 680 |
| 5 | 5.1 | 6.8 | 42 | 41 | 470 | 778 |
| 6 | 5.5 | 3.7 | 45 | 38 | 460 | 395 |
| 7 | 5.8 | 3.6 | 30 | 37 | 600 | 690 |
| 8 | 5.1 | 4.4 | 35 | 39 | 710 | 676 |
| 9 | 5.5 | 4.1 | 39 | 42 | 820 | 518 |
| 10 | 4.9 | 3.9 | 38 | 40 | 537 | 672 |
| 11 | 5.0 | 3.5 | 41 | 40 | 645 | 535 |
| 12 | 5.2 | 4.3 | 38 | 42 | 640 | 690 |
| 13 | 6.5 | 3.5 | 41 | 38 | 675 | 535 |
| 14 | 6.1 | 4.0 | 46 | 38 | 370 | 720 |
| 15 | 4.7 | 4.8 | 38 | 39 | 690 | 690 |
| 16 | 4.3 | 5.1 | 38 | 40 | 340 | 642 |
| 17 | 5.3 | 3.6 | 41 | 40 | 820 | 781 |
| 18 | 4.9 | 4.3 | 39 | 42 | 660 | 635 |
| 19 | 5.6 | 5.1 | 38 | 37 | 750 | 520 |
| 20 | 6.0 | 3.7 | 34 | 41 | 555 | 810 |
| 21 | 6.2 | 5.6 | 38 | 41 | 660 | 778 |
| 22 | 4.6 | 4.0 | 38 | 43 | 580 | 685 |
| 23 | 4.8 | 4.8 | 32 | 43 | 734 | 763 |
| 24 | 5.2 | 4.0 | 40 | 44 | 695 | 895 |
| Average | 5.3 | 4.5 | 38.4 | 40.0 | 609.6 | 684.1 |
| Stan dev | 0.63 | 0.85 | 3.56 | 2.46 | 129.30 | 124.92 |
| T test | 3.64E-04 | | 7.23E-02 | | 4.83E-02 | |

We claim:

1. Lettuce seed having ATCC Accession Number PTA-4008.

2. A lettuce plant produced by growing the seed of claim 1.

3. A lettuce plant having all the physiological and morphological characteristics of the lettuce plant of claim 2.

4. A method of making an $F_1$ hybrid lettuce plant consisting of crossing Sun Devil as a first lettuce parent plant with a second lettuce parent plant, wherein Sun Devil is grown from the seed of claim 1; harvesting the resultant $F_1$ hybrid seed; and growing an $F_1$ hybrid seed into an $F_1$ hybrid lettuce plant.

5. Pollen of the plant of claim 2.

6. An ovule of the plant of claim 2.

7. Tissue culture of the plant of claim 2.

* * * * *